United States Patent
Zhao et al.

(10) Patent No.: US 12,416,639 B2
(45) Date of Patent: Sep. 16, 2025

(54) REAGENTS AND METHODS FOR DETECTING PROTEIN LYSINE LACTYLATION

(71) Applicant: Jingjie PTM Biolab (Hangzhou) Co., Inc, Hangzhou (CN)

(72) Inventors: Yingming Zhao, Chicago, IL (US); Di Zhang, Hangzhou (CN); Lunzhi Dai, Chicago, IL (US)

(73) Assignee: Jingjie PTM Biolab (Hangzhou) Co., Inc., Hangzhou (CN)

( * ) Notice: Subject to any disclaimer, the term of this patent is extended or adjusted under 35 U.S.C. 154(b) by 1123 days.

(21) Appl. No.: 17/416,955

(22) PCT Filed: Dec. 19, 2019

(86) PCT No.: PCT/US2019/067509
§ 371 (c)(1),
(2) Date: Jun. 21, 2021

(87) PCT Pub. No.: WO2020/132260
PCT Pub. Date: Jun. 25, 2020

(65) Prior Publication Data
US 2022/0091129 A1     Mar. 24, 2022

Related U.S. Application Data

(60) Provisional application No. 62/783,926, filed on Dec. 21, 2018.

(51) Int. Cl.
*G01N 33/68* (2006.01)

(52) U.S. Cl.
CPC .............................. *G01N 33/6812* (2013.01)

(58) Field of Classification Search
CPC ........ C07K 14/43545; C07K 14/43581; C07K 14/47; G01N 2440/00; G01N 33/6812; G01N 33/6875
See application file for complete search history.

(56) References Cited

U.S. PATENT DOCUMENTS

| 2004/0115768 A1 | 6/2004 | Follstad |
| 2008/0108139 A1 | 5/2008 | Rabbani et al. |
| 2013/0116146 A1 | 5/2013 | Wang et al. |
| 2016/0002306 A1 | 1/2016 | Huang et al. |

OTHER PUBLICATIONS

Zhang et al., "Metabolic regulation of gene expression by histone lactylation," Nature, 2019, vol. 574, pp. 575-580.*
Izzo et al., "Lactate links metabolism to genes," Nature, 2019, vol. 574, (7779), p. 492-493.*
Almagro et al., "Humanization of Antibodies", Frontiers in Bioscience, 2008, vol. 13, pp. 1619-1633.*
Goel et al., "Plasticity within the Antigen Combining Site May Manifest as Molecular Mimicry in the Humoral Immune Response", J. Immunol., 2004, vol. 173, No. 12, pp. 7358-7367.*
Edwards et al., "The remarkable flexibility of the human antibody repertoire; isolation of over one thousand different antibodies to a single protein, BLyS," J. Mol. Biol., 2003, vol. 334, pp. 103-118.*
Lloyd et al., "Modelling the human immune response: performance of a 10e11 human antibody repertoire against a broad panel of therapeutically relevant antigens," Protein Engineering, Design and Selection, 2009, vol. 22, issue 3, pp. 159-168.*
Brown et al., "Tolerance of single, but not multiple, amino acid replacements in antibody Vh Cdr 2: a means of minimizing B cell wastage from somatic hypermutation?", J. Immunol., 1996 vol. 156, No. 9, pp. 3285-3291.*
Vajdos et al., "Comprehensive functional maps of the antigen-binding site of an anti-ErbB2 antibody obtained with shotgun scanning mutagenesis," J. Mol. Biol., 2002, vol. 320, No. 2, pp. 415-428.*
Rigby et al., "Methods for the analysis of histone H3 and H4 acetylation in blood," Epigenetics, 2012, vol. 7, No. 8, pp. 875-882.*
Cuddapah et al., "Native Chromatin Preparation and Ilumina/Solexa Library Construction", Cold Spring Harb Protoc., 2009; 4(6), 8 pages.
International Preliminary Report for International Application No. PCT/US2019/067509, dated Jun. 16, 2021, 7 pages.
International Search Report and Written Opinion for International Application No. PCT/US2019/067509, dated May 5, 2020, 11 pages.
Lui et al., *Acetate production from glucose and coupling to mitochondrial metabolism in mammals*, Cell, Oct. 4, 2018; 175(2):502-513.
Schechter et al., *Extraction, purification and analysis of histones*, Nature Protocols, vol. 2, No. 6, 2007, pp. 1445-1457.
Tang et al., *SET1 and p300 Act Synergistically, through Coupled Histone Modifications, in Transcriptional Activation by p53*, Cell., Jul. 18, 2013; 154(2):297-310.

\* cited by examiner

*Primary Examiner* — Galina M. Yakovleva
(74) *Attorney, Agent, or Firm* — Buchanan Ingersoll & Rooney PC

(57) ABSTRACT

The invention provides an isolated peptide comprising a lactylated lysine and a specific affinity reagent that specifically binds to a lactylated lysine in a peptide. Also provided are a method for detecting a lactylated lysine in a protein or a fragment thereof using the affinity reagent and a method for isolating the affinity reagent.

6 Claims, 3 Drawing Sheets
Specification includes a Sequence Listing.

US 12,416,639 B2

SEQUENCE LISTING

```
<160> NUMBER OF SEQ ID NOS: 132

<210> SEQ ID NO 1
<211> LENGTH: 213
<212> TYPE: PRT
<213> ORGANISM: Homo sapiens

<400> SEQUENCE: 1

Met Ser Glu Thr Ala Pro Ala Ala Pro Ala Ala Ala Pro Pro Ala Glu
1               5                   10                  15

Lys Ala Pro Val Lys Lys Lys Ala Ala Lys Lys Ala Gly Gly Thr Pro
            20                  25                  30

Arg Lys Ala Ser Gly Pro Pro Val Ser Glu Leu Ile Thr Lys Ala Val
        35                  40                  45

Ala Ala Ser Lys Glu Arg Ser Gly Val Ser Leu Ala Ala Leu Lys Lys
    50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Thr Leu Val Gln Thr
```

```
                    85                  90                  95
Lys Gly Thr Gly Ala Ser Gly Ser Phe Lys Leu Asn Lys Lys Ala Ala
                100                 105                 110

Ser Gly Glu Ala Lys Pro Lys Val Lys Lys Ala Gly Gly Thr Lys Pro
                115                 120                 125

Lys Lys Pro Val Gly Ala Ala Lys Lys Pro Lys Lys Ala Ala Gly Gly
        130                 135                 140

Ala Thr Pro Lys Lys Ser Ala Lys Lys Thr Pro Lys Lys Ala Lys Lys
145                 150                 155                 160

Pro Ala Ala Ala Thr Val Thr Lys Lys Val Ala Lys Ser Pro Lys Lys
                165                 170                 175

Ala Lys Val Ala Lys Pro Lys Lys Ala Ala Lys Ser Ala Ala Lys Ala
                180                 185                 190

Val Lys Pro Lys Ala Ala Lys Pro Lys Val Val Lys Pro Lys Lys Ala
        195                 200                 205

Ala Pro Lys Lys Lys
        210

<210> SEQ ID NO 2
<211> LENGTH: 130
<212> TYPE: PRT
<213> ORGANISM: Homo sapiens

<400> SEQUENCE: 2

Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
                20                  25                  30

Arg Leu Leu Arg Lys Gly Asn Tyr Ala Glu Arg Val Gly Ala Gly Ala
            35                  40                  45

Pro Val Tyr Leu Ala Ala Val Leu Glu Tyr Leu Thr Ala Glu Ile Leu
        50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Lys Val Thr Ile Ala Gln Gly Gly Val Leu Pro Asn Ile
                100                 105                 110

Gln Ala Val Leu Leu Pro Lys Lys Thr Glu Ser His His Lys Ala Lys
            115                 120                 125

Gly Lys
    130

<210> SEQ ID NO 3
<211> LENGTH: 126
<212> TYPE: PRT
<213> ORGANISM: Homo sapiens

<400> SEQUENCE: 3

Met Pro Glu Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
                20                  25                  30

Ser Arg Lys Glu Ser Tyr Ser Val Tyr Val Tyr Lys Val Leu Lys Gln
            35                  40                  45

Val His Pro Asp Thr Gly Ile Ser Ser Lys Ala Met Gly Ile Met Asn
```

```
                50                  55                  60
Ser Phe Val Asn Asp Ile Phe Glu Arg Ile Ala Gly Glu Ala Ser Arg
 65                  70                  75                  80

Leu Ala His Tyr Asn Lys Arg Ser Thr Ile Thr Ser Arg Glu Ile Gln
                 85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125

<210> SEQ ID NO 4
<211> LENGTH: 136
<212> TYPE: PRT
<213> ORGANISM: Homo sapiens

<400> SEQUENCE: 4

Met Ala Arg Thr Lys Gln Thr Ala Arg Lys Ser Thr Gly Gly Lys Ala
 1               5                  10                  15

Pro Arg Lys Gln Leu Ala Thr Lys Ala Ala Arg Lys Ser Ala Pro Ser
                20                  25                  30

Thr Gly Gly Val Lys Lys Pro His Arg Tyr Arg Pro Gly Thr Val Ala
             35                  40                  45

Leu Arg Glu Ile Arg Arg Tyr Gln Lys Ser Thr Glu Leu Leu Ile Arg
         50                  55                  60

Lys Leu Pro Phe Gln Arg Leu Val Arg Glu Ile Ala Gln Asp Phe Lys
 65                  70                  75                  80

Thr Asp Leu Arg Phe Gln Ser Ala Ala Ile Gly Ala Leu Gln Glu Ala
                 85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
        130                 135

<210> SEQ ID NO 5
<211> LENGTH: 103
<212> TYPE: PRT
<213> ORGANISM: Homo sapiens

<400> SEQUENCE: 5

Met Ser Gly Arg Gly Lys Gly Gly Lys Gly Leu Gly Lys Gly Gly Ala
 1               5                  10                  15

Lys Arg His Arg Lys Val Leu Arg Asp Asn Ile Gln Gly Ile Thr Lys
                20                  25                  30

Pro Ala Ile Arg Arg Leu Ala Arg Arg Gly Gly Val Lys Arg Ile Ser
             35                  40                  45

Gly Leu Ile Tyr Glu Glu Thr Arg Gly Val Leu Lys Val Phe Leu Glu
         50                  55                  60

Asn Val Ile Arg Asp Ala Val Thr Tyr Thr Glu His Ala Lys Arg Lys
 65                  70                  75                  80

Thr Val Thr Ala Met Asp Val Val Tyr Ala Leu Lys Arg Gln Gly Arg
                 85                  90                  95

Thr Leu Tyr Gly Phe Gly Gly
            100
```

<210> SEQ ID NO 6
<211> LENGTH: 212
<212> TYPE: PRT
<213> ORGANISM: Mus musculus

<400> SEQUENCE: 6

Met Ser Glu Ala Ala Pro Ala Ala Pro Ala Ala Pro Pro Ala Glu
1               5                   10                  15

Lys Ala Pro Ala Lys Lys Lys Ala Ala Lys Lys Pro Ala Gly Val Arg
            20                  25                  30

Arg Lys Ala Ser Gly Pro Pro Val Ser Glu Leu Ile Thr Lys Ala Val
        35                  40                  45

Ala Ala Ser Lys Glu Arg Ser Gly Val Ser Leu Ala Ala Leu Lys Lys
    50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Ile Leu Val Gln Thr
                85                  90                  95

Lys Gly Thr Gly Ala Ser Gly Ser Phe Lys Leu Asn Lys Lys Ala Ala
            100                 105                 110

Ser Gly Glu Ala Lys Pro Gln Ala Lys Lys Ala Gly Ala Ala Lys Ala
        115                 120                 125

Lys Lys Pro Ala Gly Ala Ala Lys Lys Pro Lys Lys Ala Thr Gly Ala
    130                 135                 140

Ala Thr Pro Lys Lys Ala Ala Lys Lys Thr Pro Lys Lys Ala Lys Lys
145                 150                 155                 160

Pro Ala Ala Ala Val Thr Lys Lys Val Ala Lys Ser Pro Lys Lys
                165                 170                 175

Ala Lys Val Thr Lys Pro Lys Lys Val Lys Ser Ala Ser Lys Ala Val
            180                 185                 190

Lys Pro Lys Ala Ala Lys Pro Lys Val Ala Lys Ala Lys Val Ala
        195                 200                 205

Ala Lys Lys Lys
    210

<210> SEQ ID NO 7
<211> LENGTH: 130
<212> TYPE: PRT
<213> ORGANISM: Mus musculus

<400> SEQUENCE: 7

Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ser Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Arg Val Thr Ile Ala Gln Gly Gly Val Leu Pro Asn Ile
            100                 105                 110

Gln Ala Val Leu Leu Pro Lys Lys Thr Glu Ser His His Lys Ala Lys

```
                 115                 120                 125

Gly Lys
    130

<210> SEQ ID NO 8
<211> LENGTH: 126
<212> TYPE: PRT
<213> ORGANISM: Mus musculus

<400> SEQUENCE: 8

Met Pro Glu Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
            20                  25                  30

Ser Arg Lys Glu Ser Tyr Ser Val Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Ser Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125

<210> SEQ ID NO 9
<211> LENGTH: 136
<212> TYPE: PRT
<213> ORGANISM: Mus musculus

<400> SEQUENCE: 9

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 10
<211> LENGTH: 103
<212> TYPE: PRT
<213> ORGANISM: Mus musculus

<400> SEQUENCE: 10
```

```
Met Ser Gly Arg Gly Lys Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
            35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100
```

<210> SEQ ID NO 11
<211> LENGTH: 132
<212> TYPE: PRT
<213> ORGANISM: Saccharomyces cerevisiae

<400> SEQUENCE: 11

```
Met Ser Gly Gly Lys Gly Gly Lys Ala Gly Ser Ala Ala Lys Ala Ser
1               5                   10                  15

Gln Ser Arg Ser Ala Lys Ala Gly Leu Thr Phe Pro Val Gly Arg Val
            20                  25                  30

His Arg Leu Leu Arg Arg Gly Asn Tyr Ala Gln Arg Ile Gly Ser Gly
            35                  40                  45

Ala Pro Val Tyr Leu Thr Ala Val Leu Glu Tyr Leu Ala Ala Glu Ile
    50                  55                  60

Leu Glu Leu Ala Gly Asn Ala Ala Arg Asp Asn Lys Lys Thr Arg Ile
65                  70                  75                  80

Ile Pro Arg His Leu Gln Leu Ala Ile Arg Asn Asp Asp Glu Leu Asn
            85                  90                  95

Lys Leu Leu Gly Asn Val Thr Ile Ala Gln Gly Gly Val Leu Pro Asn
            100                 105                 110

Ile His Gln Asn Leu Leu Pro Lys Lys Ser Ala Lys Ala Thr Lys Ala
        115                 120                 125

Ser Gln Glu Leu
    130
```

<210> SEQ ID NO 12
<211> LENGTH: 131
<212> TYPE: PRT
<213> ORGANISM: Saccharomyces cerevisiae

<400> SEQUENCE: 12

```
Met Ser Ser Ala Ala Glu Lys Lys Pro Ala Ser Lys Ala Pro Ala Glu
1               5                   10                  15

Lys Lys Pro Ala Ala Lys Lys Thr Ser Thr Ser Val Asp Gly Lys Lys
            20                  25                  30

Arg Ser Lys Val Arg Lys Glu Thr Tyr Ser Ser Tyr Ile Tyr Lys Val
            35                  40                  45

Leu Lys Gln Thr His Pro Asp Thr Gly Ile Ser Gln Lys Ser Met Ser
    50                  55                  60

Ile Leu Asn Ser Phe Val Asn Asp Ile Phe Glu Arg Ile Ala Thr Glu
65                  70                  75                  80
```

```
Ala Ser Lys Leu Ala Ala Tyr Asn Lys Lys Ser Thr Ile Ser Ala Arg
                85                  90                  95

Glu Ile Gln Thr Ala Val Arg Leu Ile Leu Pro Gly Glu Leu Ala Lys
            100                 105                 110

His Ala Val Ser Glu Gly Thr Arg Ala Val Thr Lys Tyr Ser Ser Ser
        115                 120                 125

Thr Gln Ala
    130

<210> SEQ ID NO 13
<211> LENGTH: 136
<212> TYPE: PRT
<213> ORGANISM: Saccharomyces cerevisiae

<400> SEQUENCE: 13

Met Ala Arg Thr Lys Gln Thr Ala Arg Lys Ser Thr Gly Gly Lys Ala
1               5                   10                  15

Pro Arg Lys Gln Leu Ala Ser Lys Ala Ala Arg Lys Ser Ala Pro Ser
            20                  25                  30

Thr Gly Gly Val Lys Lys Pro His Arg Tyr Lys Pro Gly Thr Val Ala
        35                  40                  45

Leu Arg Glu Ile Arg Arg Phe Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Ile Gly Ala Leu Gln Glu Ser
                85                  90                  95

Val Glu Ala Tyr Leu Val Ser Leu Phe Glu Asp Thr Asn Leu Ala Ala
            100                 105                 110

Ile His Ala Lys Arg Val Thr Ile Gln Lys Lys Asp Ile Lys Leu Ala
        115                 120                 125

Arg Arg Leu Arg Gly Glu Arg Ser
    130                 135

<210> SEQ ID NO 14
<211> LENGTH: 103
<212> TYPE: PRT
<213> ORGANISM: Saccharomyces cerevisiae

<400> SEQUENCE: 14

Met Ser Gly Arg Gly Lys Gly Gly Lys Gly Leu Gly Lys Gly Gly Ala
1               5                   10                  15

Lys Arg His Arg Lys Ile Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Val Arg Ala Val Leu Lys Ser Phe Leu Glu
    50                  55                  60

Ser Val Ile Arg Asp Ser Val Thr Tyr Thr Glu His Ala Lys Arg Lys
65                  70                  75                  80

Thr Val Thr Ser Leu Asp Val Val Tyr Ala Leu Lys Arg Gln Gly Arg
                85                  90                  95

Thr Leu Tyr Gly Phe Gly Gly
            100

<210> SEQ ID NO 15
```

<211> LENGTH: 133
<212> TYPE: PRT
<213> ORGANISM: Tetrahymena thermophila

<400> SEQUENCE: 15

Met Ser Thr Thr Gly Lys Gly Lys Ala Lys Gly Lys Thr Ala Ser
1               5                   10                  15

Ser Lys Gln Val Ser Arg Ser Ala Arg Ala Gly Leu Gln Phe Pro Val
                20                  25                  30

Gly Arg Ile Ser Arg Phe Leu Lys Asn Gly Arg Tyr Ser Glu Arg Ile
                35                  40                  45

Gly Thr Gly Ala Pro Val Tyr Leu Ala Ala Val Leu Glu Tyr Leu Ala
            50                  55                  60

Ala Glu Val Leu Glu Leu Ala Gly Asn Ala Ala Lys Asp Asn Lys Lys
65                  70                  75                  80

Thr Arg Ile Val Pro Arg His Ile Leu Leu Ala Ile Arg Asn Asp Glu
                85                  90                  95

Glu Leu Asn Lys Leu Met Ala Asn Thr Thr Ile Ala Asp Gly Gly Val
                100                 105                 110

Leu Pro Asn Ile Asn Pro Met Leu Leu Pro Ser Lys Thr Lys Lys Ser
            115                 120                 125

Thr Glu Pro Glu His
        130

<210> SEQ ID NO 16
<211> LENGTH: 120
<212> TYPE: PRT
<213> ORGANISM: Tetrahymena thermophila

<400> SEQUENCE: 16

Met Ala Pro Lys Lys Ala Pro Ala Ala Ala Glu Lys Lys Val Lys
1               5                   10                  15

Lys Ala Pro Thr Thr Glu Lys Lys Asn Lys Lys Lys Arg Ser Glu Thr
                20                  25                  30

Phe Ala Ile Tyr Ile Phe Lys Val Leu Lys Gln Val His Pro Asp Val
                35                  40                  45

Gly Ile Ser Lys Lys Ala Met Asn Ile Met Asn Ser Phe Ile Asn Asp
            50                  55                  60

Ser Phe Glu Arg Ile Ala Leu Glu Ser Ser Lys Leu Val Arg Phe Asn
65                  70                  75                  80

Lys Arg Arg Thr Leu Ser Ser Arg Glu Val Gln Thr Ala Val Lys Leu
                85                  90                  95

Leu Leu Pro Gly Glu Leu Ala Arg His Ala Ile Ser Glu Gly Thr Lys
                100                 105                 110

Ala Val Thr Lys Phe Ser Ser Ser
            115                 120

<210> SEQ ID NO 17
<211> LENGTH: 136
<212> TYPE: PRT
<213> ORGANISM: Tetrahymena thermophila

<400> SEQUENCE: 17

Met Ala Arg Thr Lys Gln Thr Ala Arg Lys Ser Thr Gly Ala Lys Ala
1               5                   10                  15

Pro Arg Lys Gln Leu Ala Ser Lys Ala Ala Arg Lys Ser Ala Pro Ala
                20                  25                  30

Thr Gly Gly Ile Lys Lys Pro His Arg Phe Arg Pro Gly Thr Val Ala
            35                  40                  45

Leu Arg Glu Ile Arg Lys Tyr Gln Lys Ser Thr Asp Leu Leu Ile Arg
 50                  55                  60

Lys Leu Pro Phe Gln Arg Leu Val Arg Asp Ile Ala His Glu Phe Lys
 65                  70                  75                  80

Ala Glu Leu Arg Phe Gln Ser Ser Ala Val Leu Ala Leu Gln Glu Ala
                85                  90                  95

Ala Glu Ala Tyr Leu Val Gly Leu Phe Glu Asp Thr Asn Leu Cys Ala
            100                 105                 110

Ile His Ala Arg Arg Val Thr Ile Met Thr Lys Asp Met Gln Leu Ala
            115                 120                 125

Arg Arg Ile Arg Gly Glu Arg Phe
    130                 135

<210> SEQ ID NO 18
<211> LENGTH: 103
<212> TYPE: PRT
<213> ORGANISM: Tetrahymena thermophila

<400> SEQUENCE: 18

Met Ala Gly Gly Lys Gly Gly Lys Gly Met Gly Lys Val Gly Ala Lys
 1               5                  10                  15

Arg His Ser Arg Lys Ser Asn Lys Ala Ser Ile Glu Gly Ile Thr Lys
                20                  25                  30

Pro Ala Ile Arg Arg Leu Ala Arg Arg Gly Gly Val Lys Arg Ile Ser
            35                  40                  45

Ser Phe Ile Tyr Asp Asp Ser Arg Gln Val Leu Lys Ser Phe Leu Glu
 50                  55                  60

Asn Val Val Arg Asp Ala Val Thr Tyr Thr Glu His Ala Arg Arg Lys
 65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 19
<211> LENGTH: 256
<212> TYPE: PRT
<213> ORGANISM: Drosophila melanogaster

<400> SEQUENCE: 19

Met Ser Asp Ser Ala Val Ala Thr Ser Ala Ser Pro Val Ala Ala Pro
 1               5                  10                  15

Pro Ala Thr Val Glu Lys Lys Val Gln Lys Lys Ala Ser Gly Ser
                20                  25                  30

Ala Gly Thr Lys Ala Lys Lys Ala Ser Ala Thr Pro Ser His Pro Pro
            35                  40                  45

Thr Gln Gln Met Val Asp Ala Ser Ile Lys Asn Leu Lys Glu Arg Gly
 50                  55                  60

Gly Ser Ser Leu Leu Ala Ile Lys Lys Tyr Ile Thr Ala Thr Tyr Lys
 65                  70                  75                  80

Cys Asp Ala Gln Lys Leu Ala Pro Phe Ile Lys Lys Tyr Leu Lys Ser
                85                  90                  95

Ala Val Val Asn Gly Lys Leu Ile Gln Thr Lys Gly Lys Gly Ala Ser
            100                 105                 110

Gly Ser Phe Lys Leu Ser Ala Ser Ala Lys Lys Glu Lys Asp Pro Lys
            115                 120                 125

Ala Lys Ser Lys Val Leu Ser Ala Glu Lys Val Gln Ser Lys Lys
    130                 135                 140

Val Ala Ser Lys Lys Ile Gly Val Ser Lys Lys Thr Ala Val Gly
145                 150                 155                 160

Ala Ala Asp Lys Lys Pro Lys Ala Lys Lys Ala Val Ala Thr Lys Lys
                165                 170                 175

Thr Ala Glu Asn Lys Lys Thr Glu Lys Ala Lys Ala Lys Asp Ala Lys
            180                 185                 190

Lys Thr Gly Ile Ile Lys Ser Lys Pro Ala Ala Thr Lys Ala Lys Val
    195                 200                 205

Thr Ala Ala Lys Pro Lys Ala Val Val Ala Lys Ala Ser Lys Ala Lys
    210                 215                 220

Pro Ala Val Ser Ala Lys Pro Lys Lys Thr Val Lys Lys Ala Ser Val
225                 230                 235                 240

Ser Ala Thr Ala Lys Lys Pro Lys Ala Lys Thr Thr Ala Ala Lys Lys
                245                 250                 255

<210> SEQ ID NO 20
<211> LENGTH: 141
<212> TYPE: PRT
<213> ORGANISM: Drosophila melanogaster

<400> SEQUENCE: 20

Met Ala Gly Gly Lys Ala Gly Lys Asp Ser Gly Lys Ala Lys Ala Lys
1               5                   10                  15

Ala Val Ser Arg Ser Ala Arg Ala Gly Leu Gln Phe Pro Val Gly Arg
            20                  25                  30

Ile His Arg His Leu Lys Ser Arg Thr Thr Ser His Gly Arg Val Gly
        35                  40                  45

Ala Thr Ala Ala Val Tyr Ser Ala Ala Ile Leu Glu Tyr Leu Thr Ala
    50                  55                  60

Glu Val Leu Glu Leu Ala Gly Asn Ala Ser Lys Asp Leu Lys Val Lys
65                  70                  75                  80

Arg Ile Thr Pro Arg His Leu Gln Leu Ala Ile Arg Gly Asp Glu Glu
                85                  90                  95

Leu Asp Ser Leu Ile Lys Ala Thr Ile Ala Gly Gly Gly Val Ile Pro
            100                 105                 110

His Ile His Lys Ser Leu Ile Gly Lys Lys Glu Glu Thr Val Gln Asp
        115                 120                 125

Pro Gln Arg Lys Gly Asn Val Ile Leu Ser Gln Ala Tyr
    130                 135                 140

<210> SEQ ID NO 21
<211> LENGTH: 123
<212> TYPE: PRT
<213> ORGANISM: Drosophila melanogaster

<400> SEQUENCE: 21

Met Pro Pro Lys Thr Ser Gly Lys Ala Ala Lys Lys Ala Gly Lys Ala
1               5                   10                  15

Gln Lys Asn Ile Thr Lys Thr Asp Lys Lys Lys Arg Lys Arg Lys
            20                  25                  30

Glu Ser Tyr Ala Ile Tyr Ile Tyr Lys Val Leu Lys Gln Val His Pro
        35                  40                  45

```
Asp Thr Gly Ile Ser Ser Lys Ala Met Ser Ile Met Asn Ser Phe Val
 50                  55                  60
Asn Asp Ile Phe Glu Arg Ile Ala Ala Glu Ala Ser Arg Leu Ala His
 65                  70                  75                  80
Tyr Asn Lys Arg Ser Thr Ile Thr Ser Arg Glu Ile Gln Thr Ala Val
                 85                  90                  95
Arg Leu Leu Leu Pro Gly Glu Leu Ala Lys His Ala Val Ser Glu Gly
             100                 105                 110
Thr Lys Ala Val Thr Lys Tyr Thr Ser Ser Lys
             115                 120

<210> SEQ ID NO 22
<211> LENGTH: 136
<212> TYPE: PRT
<213> ORGANISM: Drosophila melanogaster

<400> SEQUENCE: 22

Met Ala Arg Thr Lys Gln Thr Ala Arg Lys Ser Thr Gly Gly Lys Ala
 1               5                  10                  15
Pro Arg Lys Gln Leu Ala Thr Lys Ala Ala Arg Lys Ser Ala Pro Ala
                 20                  25                  30
Thr Gly Gly Val Lys Lys Pro His Arg Tyr Arg Pro Gly Thr Val Ala
             35                  40                  45
Leu Arg Glu Ile Arg Arg Tyr Gln Lys Ser Thr Glu Leu Leu Ile Arg
 50                  55                  60
Lys Leu Pro Phe Gln Arg Leu Val Arg Glu Ile Ala Gln Asp Phe Lys
 65                  70                  75                  80
Thr Asp Leu Arg Phe Gln Ser Ser Ala Val Met Ala Leu Gln Glu Ala
                 85                  90                  95
Ser Glu Ala Tyr Leu Val Gly Leu Phe Glu Asp Thr Asn Leu Cys Ala
             100                 105                 110
Ile His Ala Lys Arg Val Thr Ile Met Pro Lys Asp Ile Gln Leu Ala
             115                 120                 125
Arg Arg Ile Arg Gly Glu Arg Ala
 130                 135

<210> SEQ ID NO 23
<211> LENGTH: 103
<212> TYPE: PRT
<213> ORGANISM: Drosophila melanogaster

<400> SEQUENCE: 23

Met Thr Gly Arg Gly Lys Gly Gly Lys Gly Leu Gly Lys Gly Gly Ala
 1               5                  10                  15
Lys Arg His Arg Lys Val Leu Arg Asp Asn Ile Gln Gly Ile Thr Lys
                 20                  25                  30
Pro Ala Ile Arg Arg Leu Ala Arg Arg Gly Gly Val Lys Arg Ile Ser
             35                  40                  45
Gly Leu Ile Tyr Glu Glu Thr Arg Gly Val Leu Lys Val Phe Leu Glu
 50                  55                  60
Asn Val Ile Arg Asp Ala Val Thr Tyr Thr Glu His Ala Lys Arg Lys
 65                  70                  75                  80
Thr Val Thr Ala Met Asp Val Val Tyr Ala Leu Lys Arg Gln Gly Arg
                 85                  90                  95
Thr Leu Tyr Gly Phe Gly Gly
             100
```

```
<210> SEQ ID NO 24
<211> LENGTH: 208
<212> TYPE: PRT
<213> ORGANISM: Caenorhabditis elegans

<400> SEQUENCE: 24

Met Ser Asp Ser Ala Val Val Ala Ala Val Glu Pro Lys Val Pro
1               5                   10                  15

Lys Ala Lys Ala Ala Lys Ala Ala Lys Pro Thr Lys Val Ala Lys Ala
            20                  25                  30

Lys Ala Pro Val Ala His Pro Pro Tyr Ile Asn Met Ile Lys Glu Ala
            35                  40                  45

Ile Lys Gln Leu Lys Asp Arg Lys Gly Ala Ser Lys Gln Ala Ile Leu
        50                  55                  60

Lys Phe Ile Ser Gln Asn Tyr Lys Leu Gly Asp Asn Val Ile Gln Ile
65                  70                  75                  80

Asn Ala His Leu Arg Gln Ala Leu Lys Arg Gly Val Thr Ser Lys Ala
                85                  90                  95

Leu Val Gln Ala Ala Gly Ser Gly Ala Asn Gly Arg Phe Arg Val Pro
            100                 105                 110

Glu Lys Ala Ala Ala Lys Lys Pro Ala Ala Lys Lys Pro Ala
        115                 120                 125

Ala Ala Lys Lys Pro Ala Ala Ala Lys Lys Ala Thr Gly Glu Lys Lys
145                 150                 155                 160

Ala Lys Lys Pro Ala Ala Ala Lys Pro Lys Lys Ala Ala Thr Gly Asp
145                 150                 155                 160

Lys Lys Val Lys Lys Ala Lys Ser Pro Lys Lys Val Ala Lys Pro Ala
                165                 170                 175

Ala Lys Lys Val Ala Lys Ser Pro Ala Lys Lys Ala Ala Pro Lys Lys
            180                 185                 190

Ile Ala Lys Pro Ala Ala Lys Lys Ala Ala Lys Pro Ala Ala Lys Ala
            195                 200                 205

<210> SEQ ID NO 25
<211> LENGTH: 127
<212> TYPE: PRT
<213> ORGANISM: Caenorhabditis elegans

<400> SEQUENCE: 25

Met Ser Gly Arg Gly Lys Gly Gly Lys Ala Lys Thr Gly Gly Lys Ala
1               5                   10                  15

Lys Ser Arg Ser Arg Ala Gly Leu Gln Phe Pro Val Gly Arg Leu
            20                  25                  30

His Arg Ile Leu Arg Lys Gly Asn Tyr Ala Gln Arg Val Gly Ala Gly
            35                  40                  45

Ala Pro Val Tyr Leu Ala Ala Val Leu Glu Tyr Leu Ala Ala Glu Val
        50                  55                  60

Leu Glu Leu Ala Gly Asn Ala Ala Arg Asp Asn Lys Lys Thr Arg Ile
65                  70                  75                  80

Ala Pro Arg His Leu Gln Leu Ala Val Arg Asn Asp Glu Glu Leu Asn
                85                  90                  95

Lys Leu Leu Ala Gly Val Thr Ile Ala Gln Gly Gly Val Leu Pro Asn
            100                 105                 110

Ile Gln Ala Val Leu Leu Pro Lys Lys Thr Gly Gly Asp Lys Glu
            115                 120                 125
```

<210> SEQ ID NO 26
<211> LENGTH: 122
<212> TYPE: PRT
<213> ORGANISM: Caenorhabditis elegans

<400> SEQUENCE: 26

Met Pro Pro Lys Pro Ser Ala Lys Gly Ala Lys Lys Ala Ala Lys Thr
1               5                   10                  15

Val Thr Lys Pro Lys Asp Gly Lys Lys Arg Arg His Ala Arg Lys Glu
            20                  25                  30

Ser Tyr Ser Val Tyr Ile Tyr Arg Val Leu Lys Gln Val His Pro Asp
        35                  40                  45

Thr Gly Val Ser Ser Lys Ala Met Ser Ile Met Asn Ser Phe Val Asn
    50                  55                  60

Asp Val Phe Glu Arg Ile Ala Ala Glu Ala Ser Arg Leu Ala His Tyr
65                  70                  75                  80

Asn Lys Arg Ser Thr Ile Ser Ser Arg Glu Ile Gln Thr Ala Val Arg
                85                  90                  95

Leu Ile Leu Pro Gly Glu Leu Ala Lys His Ala Val Ser Glu Gly Thr
            100                 105                 110

Lys Ala Val Thr Lys Tyr Thr Ser Ser Lys
        115                 120

<210> SEQ ID NO 27
<211> LENGTH: 136
<212> TYPE: PRT
<213> ORGANISM: Caenorhabditis elegans

<400> SEQUENCE: 27

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Ser Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Arg Ala Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 28
<211> LENGTH: 103
<212> TYPE: PRT
<213> ORGANISM: Caenorhabditis elegans

<400> SEQUENCE: 28

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys

```
            20                  25                  30
Pro Ala Ile Arg Arg Leu Ala Arg Arg Gly Val Lys Arg Ile Ser
            35                  40                  45
Gly Leu Ile Tyr Glu Glu Thr Arg Gly Val Leu Lys Val Phe Leu Glu
        50                  55                  60
Asn Val Ile Arg Asp Ala Val Thr Tyr Cys Glu His Ala Lys Arg Lys
65                  70                  75                  80
Thr Val Thr Ala Met Asp Val Val Tyr Ala Leu Lys Arg Gln Gly Arg
                85                  90                  95
Thr Leu Tyr Gly Phe Gly Gly
                100
```

<210> SEQ ID NO 29
<211> LENGTH: 5
<212> TYPE: PRT
<213> ORGANISM: Artificial Sequence
<220> FEATURE:
<223> OTHER INFORMATION: Synthetic

<400> SEQUENCE: 29

```
Ala Arg Lys Ser Thr
1               5
```

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

```
Gln Thr Ala Arg Lys Ser Thr Gly Gly
1               5
```

<210> SEQ ID NO 31
<211> LENGTH: 5
<212> TYPE: PRT
<213> ORGANISM: Artificial Sequence
<220> FEATURE:
<223> OTHER INFORMATION: Synthetic

<400> SEQUENCE: 31

```
Gly Gly Lys Ala Pro
1               5
```

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

```
Ser Thr Gly Gly Lys Ala Pro Arg Lys
1               5
```

<210> SEQ ID NO 33
<211> LENGTH: 5
<212> TYPE: PRT
<213> ORGANISM: Artificial Sequence
<220> FEATURE:
<223> OTHER INFORMATION: Synthetic

<400> SEQUENCE: 33

```
Pro Arg Lys Gln Leu
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Lys Ala Pro Arg Lys Gln Leu Ala Thr
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic

<400> SEQUENCE: 35

Ala Thr Lys Ala Ala
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic

<400> SEQUENCE: 36

Gln Leu Ala Thr Lys Ala Ala Arg Lys
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic

<400> SEQUENCE: 37

Ala Arg Lys Ser Ala
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

Lys Ala Ala Arg Lys Ser Ala Pro Ser
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic

<400> SEQUENCE: 39

Tyr Gln Lys Ser Thr
```

```
1               5
```

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

```
Arg Arg Tyr Gln Lys Ser Thr Glu Leu
1               5
```

<210> SEQ ID NO 41
<211> LENGTH: 5
<212> TYPE: PRT
<213> ORGANISM: Artificial Sequence
<220> FEATURE:
<223> OTHER INFORMATION: Synthetic

<400> SEQUENCE: 41

```
Asp Phe Lys Thr Asp
1               5
```

<210> SEQ ID NO 42
<211> LENGTH: 9
<212> TYPE: PRT
<213> ORGANISM: Artificial Sequence
<220> FEATURE:
<223> OTHER INFORMATION: Synthetic

<400> SEQUENCE: 42

```
Ala Gln Asp Phe Lys Thr Asp Leu Arg
1               5
```

<210> SEQ ID NO 43
<211> LENGTH: 5
<212> TYPE: PRT
<213> ORGANISM: Artificial Sequence
<220> FEATURE:
<223> OTHER INFORMATION: Synthetic

<400> SEQUENCE: 43

```
Met Pro Lys Asp Ile
1               5
```

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

```
Thr Ile Met Pro Lys Asp Ile Gln Leu
1               5
```

<210> SEQ ID NO 45
<211> LENGTH: 5
<212> TYPE: PRT
<213> ORGANISM: Artificial Sequence
<220> FEATURE:
<223> OTHER INFORMATION: Synthetic

<400> SEQUENCE: 45

```
Pro Ala Lys Ser Ala
1               5
```

```
<210> SEQ ID NO 46
<211> LENGTH: 9
<212> TYPE: PRT
<213> ORGANISM: Artificial Sequence
<220> FEATURE:
<223> OTHER INFORMATION: Synthetic

<400> SEQUENCE: 46

Pro Glu Pro Ala Lys Ser Ala Pro Ala
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic

<400> SEQUENCE: 47

Ala Pro Lys Lys Gly
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Ala Pro Ala Pro Lys Lys Gly Ser Lys
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic

<400> SEQUENCE: 49

Pro Lys Lys Gly Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic

<400> SEQUENCE: 50

Pro Ala Pro Lys Lys Gly Ser Lys Lys
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic

<400> SEQUENCE: 51

Gly Ser Lys Lys Ala
1               5
```

<210> SEQ ID NO 52
<211> LENGTH: 9
<212> TYPE: PRT
<213> ORGANISM: Artificial Sequence
<220> FEATURE:
<223> OTHER INFORMATION: Synthetic

<400> SEQUENCE: 52

Lys Lys Gly Ser Lys Lys Ala Val Thr
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic

<400> SEQUENCE: 53

Ser Lys Lys Ala Val
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic

<400> SEQUENCE: 54

Lys Gly Ser Lys Lys Ala Val Thr Lys
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic

<400> SEQUENCE: 55

Val Thr Lys Ala Gln
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic

<400> SEQUENCE: 56

Lys Ala Val Thr Lys Ala Gln Lys Lys
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic

<400> SEQUENCE: 57

Ala Gln Lys Lys Asp
1               5

```
<210> SEQ ID NO 58
<211> LENGTH: 9
<212> TYPE: PRT
<213> ORGANISM: Artificial Sequence
<220> FEATURE:
<223> OTHER INFORMATION: Synthetic

<400> SEQUENCE: 58

Thr Lys Ala Gln Lys Lys Asp Gly Lys
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic

<400> SEQUENCE: 59

Val Tyr Lys Val Leu
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic

<400> SEQUENCE: 60

Val Tyr Val Tyr Lys Val Leu Lys Gln
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic

<400> SEQUENCE: 61

Tyr Asn Lys Arg Ser
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic

<400> SEQUENCE: 62

Ala His Tyr Asn Lys Arg Ser Thr Ile
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic

<400> SEQUENCE: 63

Leu Ala Lys His Ala
1               5

<210> SEQ ID NO 64
```

```
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gly Glu Leu Ala Lys His Ala Val Ser
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic

<400> SEQUENCE: 65

Gly Thr Lys Ala Val
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic

<400> SEQUENCE: 66

Ser Glu Gly Thr Lys Ala Val Thr Lys
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic

<400> SEQUENCE: 67

Gly Gly Lys Ala Arg
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic

<400> SEQUENCE: 68

Lys Gln Gly Gly Lys Ala Arg Ala Lys
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic

<400> SEQUENCE: 69

Leu Asn Lys Leu Leu
1               5

<210> SEQ ID NO 70
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 70

Glu Glu Leu Asn Lys Leu Leu Gly Lys
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic

<400> SEQUENCE: 71

Leu Pro Lys Lys Thr
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic

<400> SEQUENCE: 72

Val Leu Leu Pro Lys Lys Thr Glu Ser
1               5

<210> SEQ ID NO 73
<211> LENGTH: 5
<212> TYPE: PRT
<213> ORGANISM: Artificial Sequence
<220> FEATURE:
<223> OTHER INFORMATION: Synthetic

<400> SEQUENCE: 73

Arg Gly Lys Gly Gly
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic

<400> SEQUENCE: 74

Ser Gly Arg Gly Lys Gly Gly Lys Gly
1               5

<210> SEQ ID NO 75
<211> LENGTH: 5
<212> TYPE: PRT
<213> ORGANISM: Artificial Sequence
<220> FEATURE:
<223> OTHER INFORMATION: Synthetic

<400> SEQUENCE: 75

Gly Gly Lys Gly Leu
1               5

<210> SEQ ID NO 76
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 76

Gly Lys Gly Gly Lys Gly Leu Gly Lys
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic

<400> SEQUENCE: 77

Leu Gly Lys Gly Gly
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic

<400> SEQUENCE: 78

Lys Gly Leu Gly Lys Gly Gly Ala Lys
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic

<400> SEQUENCE: 79

Gly Ala Lys Arg His
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Lys Gly Gly Ala Lys Arg His Arg Lys
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic

<400> SEQUENCE: 81

Ile Thr Lys Pro Ala
1               5

<210> SEQ ID NO 82
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 82

Gln Gly Ile Thr Lys Pro Ala Ile Arg
1               5

<210> SEQ ID NO 83
<211> LENGTH: 5
<212> TYPE: PRT
<213> ORGANISM: Artificial Sequence
<220> FEATURE:
<223> OTHER INFORMATION: Synthetic

<400> SEQUENCE: 83

Ala Leu Lys Arg Gln
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic

<400> SEQUENCE: 84

Val Tyr Ala Leu Lys Arg Gln Gly Arg
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic

<400> SEQUENCE: 85

Gln Leu Ala Thr Lys Ala Ala Arg
1               5

<210> SEQ ID NO 86
<211> LENGTH: 11
<212> TYPE: PRT
<213> ORGANISM: Artificial Sequence
<220> FEATURE:
<223> OTHER INFORMATION: Synthetic

<400> SEQUENCE: 86

Pro Glu Leu Ala Lys Ser Ala Pro Ala Pro Lys
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Synthetic

<400> SEQUENCE: 87

Gly Gly Lys Gly Leu Gly Lys
1               5

<210> SEQ ID NO 88
<211> LENGTH: 20
<212> TYPE: DNA
<213> ORGANISM: Artificial Sequence
<220> FEATURE:
```

<223> OTHER INFORMATION: Synthetic

<400> SEQUENCE: 88
ctgagcacac ccatgtgaga                                               20

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
agcaacactc caagtcagga                                               20

<210> SEQ ID NO 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
cccagaaatg ccagattacg                                               20

<210> SEQ ID NO 91
<211> LENGTH: 21
<212> TYPE: DNA
<213> ORGANISM: Artificial Sequence
<220> FEATURE:
<223> OTHER INFORMATION: Synthetic

<400> SEQUENCE: 91
cttgggctgc cagaatttct c                                             21

<210> SEQ ID NO 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
ttacagtcgg ccaggctgac                                               20

<210> SEQ ID NO 93
<211> LENGTH: 22
<212> TYPE: DNA
<213> ORGANISM: Artificial Sequence
<220> FEATURE:
<223> OTHER INFORMATION: Synthetic

<400> SEQUENCE: 93
ctccaagcca aagtccttag ag                                            22

<210> SEQ ID NO 94
<211> LENGTH: 22
<212> TYPE: DNA
<213> ORGANISM: Artificial Sequence
<220> FEATURE:
<223> OTHER INFORMATION: Synthetic

<400> SEQUENCE: 94
aggagctgtc attagggaca tc                                            22

```
<210> SEQ ID NO 95
<211> LENGTH: 26
<212> TYPE: DNA
<213> ORGANISM: Artificial Sequence
<220> FEATURE:
<223> OTHER INFORMATION: Synthetic

<400> SEQUENCE: 95
ccacgacaga aggagagcag aagtcc                                          26

<210> SEQ ID NO 96
<211> LENGTH: 22
<212> TYPE: DNA
<213> ORGANISM: Artificial Sequence
<220> FEATURE:
<223> OTHER INFORMATION: Synthetic

<400> SEQUENCE: 96
cgttacagca gcctgcacag cg                                              22

<210> SEQ ID NO 97
<211> LENGTH: 20
<212> TYPE: DNA
<213> ORGANISM: Artificial Sequence
<220> FEATURE:
<223> OTHER INFORMATION: Synthetic

<400> SEQUENCE: 97
gttctctggg aaatcgtgga                                                 20

<210> SEQ ID NO 98
<211> LENGTH: 20
<212> TYPE: DNA
<213> ORGANISM: Artificial Sequence
<220> FEATURE:
<223> OTHER INFORMATION: Synthetic

<400> SEQUENCE: 98
tttctgcaag tgcatcatcg                                                 20

<210> SEQ ID NO 99
<211> LENGTH: 22
<212> TYPE: DNA
<213> ORGANISM: Artificial Sequence
<220> FEATURE:
<223> OTHER INFORMATION: Synthetic

<400> SEQUENCE: 99
tttgacagtg atgagaatga cc                                              22

<210> SEQ ID NO 100
<211> LENGTH: 20
<212> TYPE: DNA
<213> ORGANISM: Artificial Sequence
<220> FEATURE:
<223> OTHER INFORMATION: Synthetic

<400> SEQUENCE: 100
ctcttgttga tgtgctgctg                                                 20

<210> SEQ ID NO 101
<211> LENGTH: 21
<212> TYPE: DNA
<213> ORGANISM: Artificial Sequence
<220> FEATURE:
<223> OTHER INFORMATION: Synthetic
```

<400> SEQUENCE: 101
cagctccaag aaaggacgaa c                                              21

<210> SEQ ID NO 102
<211> LENGTH: 21
<212> TYPE: DNA
<213> ORGANISM: Artificial Sequence
<220> FEATURE:
<223> OTHER INFORMATION: Synthetic

<400> SEQUENCE: 102
ggcagtgtaa ctcttctgca t                                              21

<210> SEQ ID NO 103
<211> LENGTH: 21
<212> TYPE: DNA
<213> ORGANISM: Artificial Sequence
<220> FEATURE:
<223> OTHER INFORMATION: Synthetic

<400> SEQUENCE: 103
ccaagtgctg ccgtcatttt c                                              21

<210> SEQ ID NO 104
<211> LENGTH: 21
<212> TYPE: DNA
<213> ORGANISM: Artificial Sequence
<220> FEATURE:
<223> OTHER INFORMATION: Synthetic

<400> SEQUENCE: 104
ggctcgcagg gatgatttca a                                              21

<210> SEQ ID NO 105
<211> LENGTH: 23
<212> TYPE: DNA
<213> ORGANISM: Artificial Sequence
<220> FEATURE:
<223> OTHER INFORMATION: Synthetic

<400> SEQUENCE: 105
ccctcacact cagatcatct tct                                            23

<210> SEQ ID NO 106
<211> LENGTH: 19
<212> TYPE: DNA
<213> ORGANISM: Artificial Sequence
<220> FEATURE:
<223> OTHER INFORMATION: Synthetic

<400> SEQUENCE: 106
gctacgacgt gggctacag                                                 19

<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
cagtgagtgt gtgcagcttg                                                20

<210> SEQ ID NO 108
<211> LENGTH: 20

```
<212> TYPE: DNA
<213> ORGANISM: Artificial Sequence
<220> FEATURE:
<223> OTHER INFORMATION: Synthetic

<400> SEQUENCE: 108
aaagcctcct gtttgtgctt                                               20

<210> SEQ ID NO 109
<211> LENGTH: 19
<212> TYPE: DNA
<213> ORGANISM: Artificial Sequence
<220> FEATURE:
<223> OTHER INFORMATION: Synthetic

<400> SEQUENCE: 109
tgcacacaga agccagaag                                                19

<210> SEQ ID NO 110
<211> LENGTH: 19
<212> TYPE: DNA
<213> ORGANISM: Artificial Sequence
<220> FEATURE:
<223> OTHER INFORMATION: Synthetic

<400> SEQUENCE: 110
gctccccaca gagacgtaa                                                19

<210> SEQ ID NO 111
<211> LENGTH: 20
<212> TYPE: DNA
<213> ORGANISM: Artificial Sequence
<220> FEATURE:
<223> OTHER INFORMATION: Synthetic

<400> SEQUENCE: 111
taagggtggg ggatacctct                                               20

<210> SEQ ID NO 112
<211> LENGTH: 20
<212> TYPE: DNA
<213> ORGANISM: Artificial Sequence
<220> FEATURE:
<223> OTHER INFORMATION: Synthetic

<400> SEQUENCE: 112
cccaagagaa aaatgcaagc                                               20

<210> SEQ ID NO 113
<211> LENGTH: 20
<212> TYPE: DNA
<213> ORGANISM: Artificial Sequence
<220> FEATURE:
<223> OTHER INFORMATION: Synthetic

<400> SEQUENCE: 113
aagctgtggc ctcagaacat                                               20

<210> SEQ ID NO 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
```

```
ggtaaccgct gtgaaaggat                                               20

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
cccgagtttg acccgaagaa                                               20

<210> SEQ ID NO 116
<211> LENGTH: 20
<212> TYPE: DNA
<213> ORGANISM: Artificial Sequence
<220> FEATURE:
<223> OTHER INFORMATION: Synthetic

<400> SEQUENCE: 116
ctttacacag ggaccggacc                                               20

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
tgtctctccc agtttcccca                                               20

<210> SEQ ID NO 118
<211> LENGTH: 21
<212> TYPE: DNA
<213> ORGANISM: Artificial Sequence
<220> FEATURE:
<223> OTHER INFORMATION: Synthetic

<400> SEQUENCE: 118
agcaacttgg catctgatgg a                                             21

<210> SEQ ID NO 119
<211> LENGTH: 20
<212> TYPE: DNA
<213> ORGANISM: Artificial Sequence
<220> FEATURE:
<223> OTHER INFORMATION: Synthetic

<400> SEQUENCE: 119
cgagctagca cttctcccag                                               20

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
aacttctggg ctcttctcgc                                               20

<210> SEQ ID NO 121
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 121
ggcaccaaat tgtggcact                                            20

<210> SEQ ID NO 122
<211> LENGTH: 20
<212> TYPE: DNA
<213> ORGANISM: Artificial Sequence
<220> FEATURE:
<223> OTHER INFORMATION: Synthetic

<400> SEQUENCE: 122
ctgccagact acacagtgca                                           20

<210> SEQ ID NO 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
acctgatcct gatccctgct                                           20

<210> SEQ ID NO 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
cagcctctgt tatgccacga                                           20

<210> SEQ ID NO 125
<211> LENGTH: 20
<212> TYPE: DNA
<213> ORGANISM: Artificial Sequence
<220> FEATURE:
<223> OTHER INFORMATION: Synthetic

<400> SEQUENCE: 125
gcagaaccta ggcttcacgt                                           20

<210> SEQ ID NO 126
<211> LENGTH: 20
<212> TYPE: DNA
<213> ORGANISM: Artificial Sequence
<220> FEATURE:
<223> OTHER INFORMATION: Synthetic

<400> SEQUENCE: 126
ttgaaagggc tgacatggct                                           20

<210> SEQ ID NO 127
<211> LENGTH: 20
<212> TYPE: DNA
<213> ORGANISM: Artificial Sequence
<220> FEATURE:
<223> OTHER INFORMATION: Synthetic

<400> SEQUENCE: 127
aaggtcatca gcaaggtcgt                                           20
```

```
<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
cgtactccga gtctcacacg                                                 20

<210> SEQ ID NO 129
<211> LENGTH: 20
<212> TYPE: DNA
<213> ORGANISM: Artificial Sequence
<220> FEATURE:
<223> OTHER INFORMATION: Synthetic

<400> SEQUENCE: 129
tagatcccct ccctcttgct                                                 20

<210> SEQ ID NO 130
<211> LENGTH: 20
<212> TYPE: DNA
<213> ORGANISM: Artificial Sequence
<220> FEATURE:
<223> OTHER INFORMATION: Synthetic

<400> SEQUENCE: 130
gaacacgtag cctgctcaca                                                 20

<210> SEQ ID NO 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
ctgccagggt tgtagagagg                                                 20

<210> SEQ ID NO 132
<211> LENGTH: 20
<212> TYPE: DNA
<213> ORGANISM: Artificial Sequence
<220> FEATURE:
<223> OTHER INFORMATION: Synthetic

<400> SEQUENCE: 132
gccagatcat attggcttgg                                                 20
```

REAGENTS AND METHODS FOR DETECTING PROTEIN LYSINE LACTYLATION

CROSS-REFERENCE TO RELATED APPLICATION

This application is a U.S. national phase application of International Application No. PCT/US2019/067509, filed Dec. 19, 2019, claiming the U.S. Provisional Application No. 62/783,926, filed Dec. 21, 2018, the contents of each of which are incorporate herein by references in their entireties for all purposes.

REFERENCE TO U.S. GOVERNMENT SUPPORT

This work is supported by a grant from the National Institutes of Health (NIH) (No. DK107868). The United States has certain rights in the invention.

FIELD OF THE INVENTION

This invention relates to reagents and methods for detecting proteins having post-translational modifications. More particularly, it relates to peptides comprising a lactylated lysine, and their uses to develop reagents and methods useful for detecting protein lysine lactylation.

BACKGROUND OF THE INVENTION

The Warburg effect, originally describing augmented lactogenesis in cancer, is associated with diverse cellular processes such as angiogenesis, hypoxia, macrophage polarization, and T-cell activation. This phenomenon is intimately linked with multiple diseases including neoplasia, sepsis, and autoimmune diseases. Lactate, a compound generated during Warburg effect, is widely known as an energy source and metabolic byproduct. However, its non-metabolic functions in physiology and disease remain unknown.

There remains a need for developing reagents and methods useful for detecting post-translational modifications of histones or nonhistone proteins linked to various diseases and disorders.

SUMMARY OF THE INVENTION

The present invention relates to an affinity reagent that binds specifically a lactylated lysine in a peptide, and the preparation and uses thereof. This invention is based on the inventors' discovery of a new type of histone marks, lysine lactylation.

An isolated affinity reagent is provided. The isolated affinity reagent binds specifically to a lactylated lysine in a peptide. The peptide may be derived from a histone protein or a fragment thereof. The histone protein may be derived from an organism selected from the group consisting of human, mouse, *S. cerevisiae, Tetrahymena thermophila, D. melanogaster*, and *C. elegans*. The peptide may comprise an amino acid sequence having at least 70% identity to an amino acid sequence selected from the group consisting of SEQ ID NOs: 29-87. The peptide may comprise an amino acid sequence selected from the group consisting of SEQ ID NOs: 29-87. The peptide may comprise at least one or two amino acid residues on each of the N-terminal and C-terminal sides of the lactylated lysine. The binding of the affinity reagent to the peptide may depend on a surrounding peptide sequence of the lactylated lysine in the peptide. The affinity reagent may be a protein. The affinity reagent may be an antibody.

A method for detecting a lactylated lysine in a protein or a fragment thereof is provided. The method comprises contacting the protein or a fragment thereof with an affinity reagent, wherein the affinity reagent binds specifically to a lactylated lysine in a peptide, whereby a binding complex of the protein or a fragment thereof and the affinity reagent is formed; and detecting the binding complex, wherein the presence of the binding complex indicates the presence of a lactylated lysine in the protein or a fragment thereof. The detection method may further comprise quantifying the lactylated lysine in the protein or a fragment thereof.

According to the detection method, the peptide may be derived from a histone protein or a fragment thereof. The histone protein may be derived from an organism selected from the group consisting of human, mouse, *S. cerevisiae, Tetrahymena thermophila, D. melanogaster*, and *C. elegans*. The peptide may comprise an amino acid sequence having at least 70% identity to an amino acid sequence selected from the group consisting of SEQ ID NOs: 29-87. The peptide may comprise an amino acid sequence selected from the group consisting of SEQ ID NOs: 29-87. The peptide may comprise at least one or two amino acid residues on each of the N-terminal and C-terminal sides of the lactylated lysine. The binding of the affinity reagent to the peptide may depend on a surrounding peptide sequence of the lactylated lysine in the peptide. The affinity reagent may be a protein. The affinity reagent may be an antibody.

A first method for isolating an affinity reagent that binds specifically to a lactylated lysine in a peptide is provided. The first isolation method comprises exposing a protein library to a peptide comprising a lactylated lysine, whereby a protein from the protein library binds specifically to the lactylated lysine and forms a binding complex with the peptide; and isolating the protein from the binding complex, whereby the isolated protein is the affinity reagent. The peptide may comprise at least one or two amino acid residues on each of the N-terminal and C-terminal sides of the lactylated lysine.

A second method for isolating an affinity reagent that binds specifically to a lactylated lysine in a peptide is provided. The second isolation method comprises immunizing a host with a peptide comprising a lactylated lysine, whereby the host produces an antibody; and isolating the antibody from the host, whereby the isolated antibody is the affinity reagent. The peptide may comprise at least one or two amino acid residues on each of the N-terminal and C-terminal sides of the lactylated lysine.

A first kit is provided. The first kit comprises an affinity reagent that binds specifically to a lactylated lysine in a peptide, and an instruction for detecting a lactylated lysine in a protein or a fragment thereof using the affinity reagent according to the detection method of the present invention.

A second kit is provided. The second kit comprises a peptide comprising a lactylated lysine, and an instruction for isolating an affinity reagent that binds specifically to the lactylated lysine in the peptide according to the first or second isolation method of the present invention.

An isolated peptide comprising a lactylated lysine is provided. The peptide may be derived from a histone protein or a fragment thereof. The histone protein may be derived from an organism selected from the group consisting of human, mouse, *S. cerevisiae, Tetrahymena thermophila, D. melanogaster*, and *C. elegans*. The peptide may comprise an amino acid sequence having at least 70% identity to an amino acid sequence selected from the group consisting of SEQ ID NOs: 29-87. The peptide may comprise an amino acid sequence selected from the group consisting of SEQ ID NOs: 29-87. The peptide may comprise at least one or two amino acid residues on each of the N-terminal and C-terminal sides of the lactylated lysine.

DETAILED DESCRIPTION OF THE INVENTION

Figure 1:
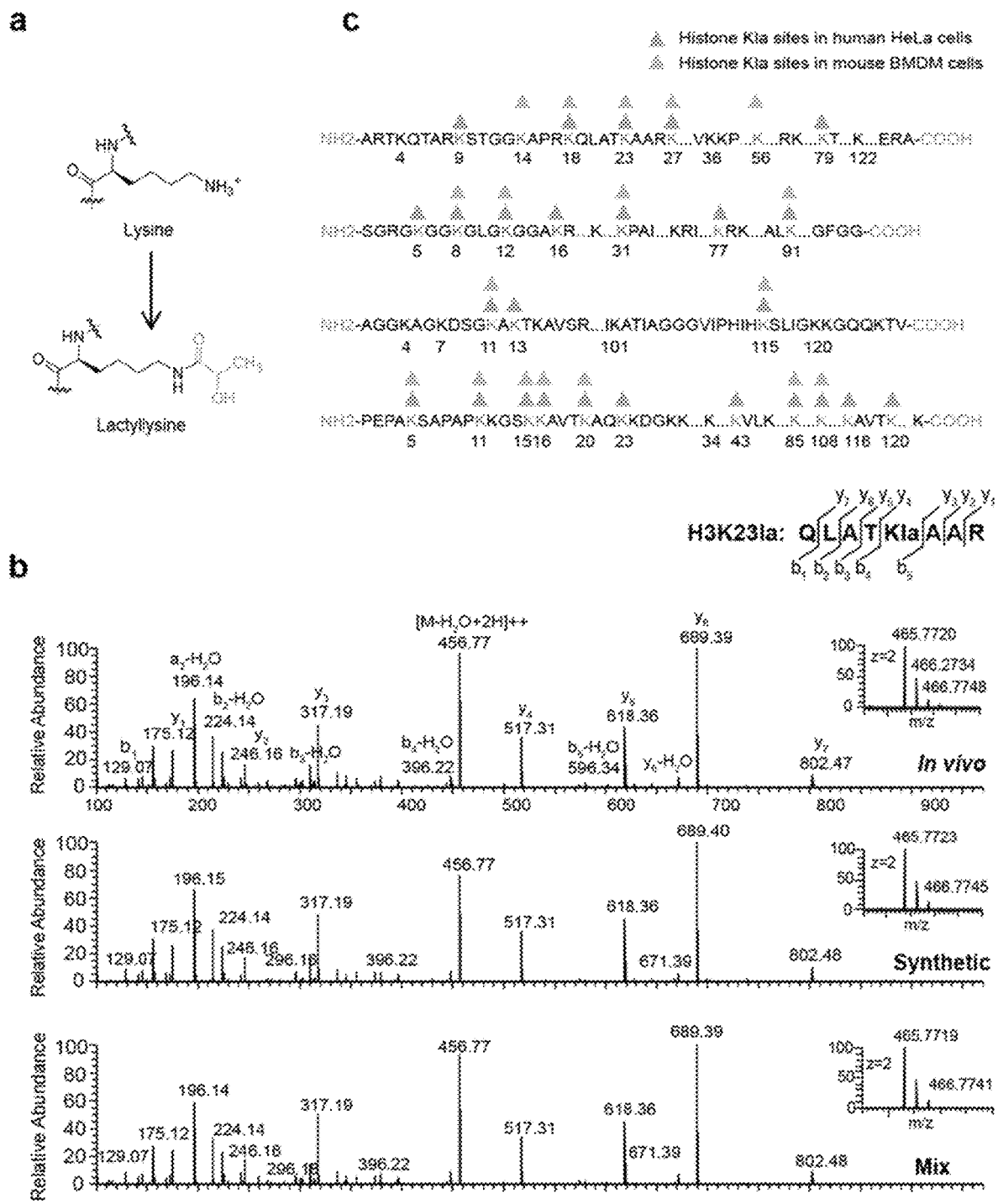
FIG. 1 shows identification and validation of histone Kla. a, Illustration of Kla structure. b, MS/MS spectra of a lactylated histone peptide (H3K23la) derived from MCF-7 cells (in vivo), its synthetic counterpart, and their mixture. b-ion refers to the amino-terminal parts of the peptide and y-ion refers to the carboxy-terminal parts of the peptide. Data represent two independent experiments. c, Illustration of histone Kla sites identified in human and mouse cells.

The present invention relates to an isolated peptides comprising a lactylated lysine, an affinity reagent that binds specifically a lactylated lysine in a peptide, and the preparation and uses thereof. The invention is based on the inventors' discovery of lactate-derived histone lysine lactylation as a new epigenetic modification and demonstration that histone lactylation directly stimulates gene transcription from chromatin. The inventors have identified 28 lactylation sites on core histones in human and mouse cells. Hypoxia and bacterial challenges induce production of lactate through glycolysis that in turn serves as precursor for stimulating histone lactylation. Using bacterially exposed M1 macrophages as a model system, the inventors have also demonstrated that histone lactylation has different temporal dynamics from acetylation. In the late phase of M1 macrophage polarization, elevated histone lactylation induces homeostatic genes involved in wound healing including arginase 1. Collectively, the results suggest the presence of an endogenous "lactate clock" in bacterially challenged M1 macrophages that turns on gene expression to promote homeostasis. Histone lactylation thus represents a new avenue for understanding the functions of lactate and its role in diverse pathophysiological conditions, including infection and cancer.

The term "peptide" used herein refers to a linear chain of two or more amino acids linked by peptide bonds. A peptide may have about 2, 3, 4, 5, 6, 7, 8, 9, 10, 11, 12, 13, 14, 15, 16, 17, 18, 19, 20, 25, 30, 40, 50, 100, 200 or more amino acids. The amino acids of a peptide may be modified, deleted, added or substituted. A peptide may be obtained using conventional techniques known in the art. For example, a peptide may be synthesized or obtained from a native or recombinant protein by enzymatic digestion.

The term "polypeptide" used herein refers to a peptide having at least four amino acids, preferably at least about 20 amino acids, regardless of post-translational modification. The term "protein" used herein refers to a biological molecule consisting of one or more polypeptides, regardless of post-translational modification. Each polypeptide in a protein may be a subunit. The polypeptide or protein may be in a native or modified form, and may exhibit a biological function or characteristics.

Where a protein is a single polypeptide, the terms "protein" and "polypeptide" are used herein interchangeably. A fragment of a polypeptide or protein refers to a portion of the polypeptide or protein having an amino acid sequence that is the same as a part, but not all, of the amino acid sequence of the polypeptide or protein. Preferably, a fragment of a polypeptide or protein exhibits a biological function or characteristics identical or similar to that of the polypeptide or protein.

The term "derived from" used herein refers to the origin or source from which a biological molecule is obtained, and may include naturally occurring, recombinant, unpurified or purified molecules. A biological molecule such as a peptide (e.g., a polypeptide or protein) may be derived from an original molecule, becoming identical to the original molecule or a variant of the original molecule. For example, a peptide derived from an original peptide may have an amino acid sequence identical or similar to the amino acid sequence of its original peptide, with at least one amino acid modified, deleted, inserted, or substituted. A derived peptide may have an amino acid sequence at least about 5%, 10%, 20%, 30%, 40%, 50%, 60%, 70%, 80%, 90%, 95%, 99% or 100%, preferably at least about 50%, more preferably at least about 80%, most preferably at least about 90%, identical to the amino acid sequence of its original peptide, regardless of post-translational modification. Preferably, a derived biological molecule (e.g., a peptide) may exhibit a biological function or characteristics identical or similar to that of the original biological molecule.

The term "antibody" used herein includes whole antibodies, and antigen binding fragments (or antigen-binding portions) and single chains thereof. A whole antibody can be either one of the two types. The first type refers to a glycoprotein typically having two heavy chains and two light chains, and includes an antigen-binding portion. For example, the antibody may be a polyclonal or monoclonal antibody. The term "antigen binding portion" of an antibody used herein refers to one or more fragments of the antibody that retain the ability of specifically binding to an antigen. The second type refers to a heavy-chain antibody occurring in camelids that is also called Nanobody. The term "single-chain variable fragment" of an antibody used herein refers to a fusion protein of the variable regions of the heavy and light chains of the antibody, connected with a short linker peptide, for example, of about 20-25 amino acids, that retains the ability of specifically binding to an antigen.

An isolated peptide comprising a lactylated lysine is provided. The term "lactylated lysine" used herein refers to a lysine residue that is modified by an L-lactyl group. The term "lysine lactylation site" used herein refers to a lysine residue in a peptide, polypeptide or protein that may be lactylated on the epsilon-amino group of the lysine residue. The term "lysine lactylation" used herein refers to lactylation on the epsilon-amino group of a lysine residue that generates a lactylated lysine.

The peptide of the present invention may have at least about 3, 4, 5, 6, 7, 8, 9, 10, 11, 12, 13, 14, 15, 16, 17, 18, 19, 20, 30, 40, 50, 60, 70, 80, 90, 100, 150 or 200 amino acids. The peptide may have about 3-25 amino acids, preferably 5-20 amino acids, more preferably 6-14 amino acids.

The peptide of the present invention may be prepared using conventional techniques known in the art. The peptide may be derived from a protein, for example, a histone protein, or a fragment thereof, having a lysine lactylation site. The histone protein may be derived from a eukaryotic cell. Examples of a eukaryotic cell include cells from a yeast (e.g., *S. cerevisiae*), a *C. elegans*, a *Drosophila* (e.g., *D. melanogaster* (S2)), a *Tetrahymena* (e.g., *Tetrahymena thermophila*), a mouse (e.g., *M. musculus* (MEF)), or a human. Preferably, the eukaryotic cell is a mammalian cell, for example, a cell from a human, primate, mouse, rat, horse, cow, pig, sheep, goat, chicken, dog or cat. More preferably, the eukaryotic cell is a human cell.

The histone protein may be a histone linker protein or a histone core protein. A histone linker protein may be selected from the members of the H1 family, including the H1F subfamily (e.g., H1F0, H1FNT, H1FOO, and H1FX) and the H1H1 subfamily (e.g., HIST1H1A, HIST1H1B, HIST1H1C, HIST1H1D, HIST1H1E and HIST1H1T). A histone core protein may a member of the H2A, H2B, H3 or H4 family. A histone core protein in the H2A family may be a member of the H2AF subfamily (e.g., H2AFB1, H2AFB2, H2AFB3, H2AFJ, H2AFV, H2AFX, H2AFY, H2AFY2, and H2AFZ), the H2A1 subfamily (e.g., HIST1H2AA, HIST1H2AB, HIST1H2AC, HIST1H2AD, HIST1H2AE, HIST1H2AG, HIST1H2AH, HIST1H2AI, HIST1H2AJ, HIST1H2AK, HIST1H2AL, and HIST1H2 AM), or the H2A2 subfamily (e.g., HIST2H2AA3, HIST2H2AA4, HIST2H2AB, and HIST2H2AC). A histone core protein in the H2B family may be a member of the H2BF subfamily (e.g., H2BFM and H2BFWT), the H2B1 subfamily (e.g., HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, and HIST1H2BO), or the H2B2 subfamily (e.g., HIST2H2BE and HIST2H2BF). A histone core protein in the H3 family may be a member of the H3A1 subfamily (e.g., HIST1H3A, HIST1H3B, HIST1H3C, HIST1H3D, HIST1H3E, HIST1H3F, HIST1H3G, HIST1H3H, HIST1H3I, and HIST1H3J), the H3A2 subfamily (e.g., HIST2H3A, HIST2H3C, and HIST2H3D), or the H3A3 subfamily (e.g., HIST3H3), the H3A3 subfamily (e.g., H3F3A, H3F3B, and H3F3C). A histone core protein in the H4 family may be a member of the H41 subfamily (e.g., HIST1H4A, HIST1H4B, HIST1H4C, HIST1H4D, HIST1H4E, HIST1H4F, HIST1H4G, HIST1H4H, HIST1H4I, HIST1H4J, HIST1H4K, and HIST1H4L), or the H44 subfamily (e.g., HIST4H4).

The protein and gene sequences of histone proteins in various species are known in the art. For example, histone protein sequences of human, mouse, *S. cerevisiae*, *Tetrahymena*, *D. melanogaster*, and *C. elegans* can be found in GenBank database Accession Nos. P16403 (H12_HUMAN) (SEQ ID NO: 1), P0C0S8 (H2A1_HUMAN) (SEQ ID NO:

2), P62807 (H2B1C_HUMAN) (SEQ ID NO: 3), P84243 (H33_HUMAN) (SEQ ID NO: 4), and P62805 (H4_HUMAN) (SEQ ID NO: 5); P15864 (H12_MOUSE) (SEQ ID NO: 6), P22752 (H2A1_MOUSE) (SEQ ID NO: 7), P10853 (H2B1F_MOUSE) (SEQ ID NO: 8), P84244 (H33_MOUSE) (SEQ ID NO: 9), and P62806 (H4_MOUSE) (SEQ ID NO: 10); P04911 (H2A1_*S. cerevisiae*) (SEQ ID NO: 11), P02294 (H2B2_*S. cerevisiae*) (SEQ ID NO: 12), P61830 (H3_*S. cerevisiae*) (SEQ ID NO: 13), and P02309 (H4_*S. cerevisiae*) (SEQ ID NO: 14); P35065 (H2A1_*Tetrahymena thermophila*) (SEQ ID NO: 15), P08993 (H2B1_*Tetrahymena thermophila*) (SEQ ID NO: 16), I7LUZ3 (H3_*Tetrahymena thermophila*) (SEQ ID NO: 17), and P69152 (H4_*Tetrahymena thermophila*) (SEQ ID NO: 18); P02255 (H1_*D. melanogaster*) (SEQ ID NO: 19), P08985 (H2AV_*D. melanogaster*) (SEQ ID NO: 20), P02283 (H2B_*D. melanogaster*) (SEQ ID NO: 21), P02299 (H3) (SEQ ID NO: 22), and P84040 (H4_*D. melanogaster*) (SEQ ID NO: 23); P10771 (H11_*C. elegans*) (SEQ ID NO: 24), P09855 (H2A_*C. elegans*) (SEQ ID NO: 25), P04255 (H2B1_*C. elegans*) (SEQ ID NO: 26), P08898 (H3_*C. elegans*) (SEQ ID NO: 27), and P62784 (H4_*C. elegans*) (SEQ ID NO: 28).

A fragment of a histone protein may have an amino acid sequence that is the same as a part, not all, of the amino acid sequence of the histone protein comprising at least one lysine lactylation site. The histone protein fragment may have at least about 1, 2, 3, 4, 5, 6, 7, 8, 9, 10, 11, 12, 13, 14, 15, 16, 17, 18, 19, 20, 30, 40, 50, 60, 70, 80, 90, 100, 150 or 200 amino acids. The histone fragment may have about 3-25 contiguous amino acids, preferably about 5-20 contiguous amino acids, more preferably about 6-14 contiguous amino acids, of the histone protein covering at least one lysine lactylation site in the histone protein. The lactylation site may be lactylated or not. Table 1 provides exemplary peptides comprising a lactylated lysine.

TABLE 1

Exemplary peptides comprising a lactylated lysine (Kla)

| Sequence | SEQ ID NO | Sequence | SEQ ID NO |
|---|---|---|---|
| AR(Kla)ST | 29 | QTAR(Kla)STGG | 30 |
| GG(Kla)AP | 31 | STGG(Kla)APRK | 32 |
| PR(Kla)QL | 33 | KAPR(Kla)QLAT | 34 |
| AT(Kla)AA | 35 | QLAT(Kla)AARK | 36 |
| AR(Kla)SA | 37 | KAAR(Kla)SAPS | 38 |
| YQ(Kla)ST | 39 | RRYQ(Kla)STEL | 40 |
| DF(Kla)TD | 41 | AQDF(Kla)TDLR | 42 |
| MP(Kla)DI | 43 | TIMP(Kla)DIQL | 44 |
| PA(Kla)SA | 45 | PEPA(Kla)SAPA | 46 |
| AP(Kla)KG | 47 | APAP(Kla)KGSK | 48 |
| PK(Kla)GS | 49 | PAPK(Kla)GSKK | 50 |
| GS(Kla)KA | 51 | KKGS(Kla)KAVT | 52 |
| SK(Kla)AV | 53 | KGSK(Kla)AVTK | 54 |
| VT(Kla)AQ | 55 | KAVT(Kla)AQKK | 56 |
| AQ(Kla)KD | 57 | TKAQ(Kla)KDGK | 58 |

TABLE 1-continued

Exemplary peptides comprising a lactylated lysine (Kla)

| Sequence | SEQ ID NO | Sequence | SEQ ID NO |
|---|---|---|---|
| VY(Kla)VL | 59 | VYVY(Kla)VLKQ | 60 |
| YN(Kla)RS | 61 | AHYN(Kla)RSTI | 62 |
| LA(Kla)HA | 63 | GELA(Kla)HAVS | 64 |
| GT(Kla)AV | 65 | SEGT(Kla)AVTK | 66 |
| GG(Kla)AR | 67 | KQGG(Kla)ARAK | 68 |
| LN(Kla)LL | 69 | EELN(Kla)LLGK | 70 |
| LP(Kla)KT | 71 | VLLP(Kla)KTES | 72 |
| RG(Kla)GG | 73 | SGRG(Kla)GGKG | 74 |
| GG(Kla)GL | 75 | GKGG(Kla)GLGK | 76 |
| LG(Kla)GG | 77 | KGLG(Kla)GGAK | 78 |
| GA(Kla)RH | 79 | KGGA(Kla)RHRK | 80 |
| IT(Kla)PA | 81 | QGIT(Kla)PAIR | 82 |
| AL(Kla)RQ | 83 | VYAL(Kla)RQGR | 84 |

The peptide may be an antigenic or bait peptide. The antigenic or bait peptide may comprise a five-residue sequence as set forth in Table 1. The antigenic or bait peptide may comprise four continuous residues of any one of the five-residue sequences in Table 1. The antigenic or bait peptide may comprise at least six continuous residues of any one of the nine-residue sequences as set forth in Table 1.

A histone protein may be obtained from a biological sample or prepared using recombinant techniques. A histone protein fragment may be prepared by recombinant techniques, or by digesting the histone protein with an enzyme (e.g., trypsin). The lysine lactylation site in the histone protein or fragment may be lysine lactylated naturally or artificially. The presence of a lactylated lysine may be confirmed by using conventional techniques known in the art, for example, mass spectrometry.

The peptide of the present invention may comprise an amino acid sequence having at least about 70%, 80%, 90%, 95% or 99%, preferably at least about 90%, more preferably 100%, identity to an amino acid sequence set forth in Table 1. The peptide may encompass any lysine lactylation site with or without its surrounding sequences from a histone protein. The peptide may comprise more than one lactylated lysine. The peptide may also comprise a protein post-translational modification other than lysine lactylation, such as lysine acetylation or methylation. The peptides may further comprise at least about 1, 2, 3, 4, 5, 6, 7, 8, 9, 10 or more residues on either or both of N-terminal and C-terminal sides of the lactylated lysine. Preferably, the peptide may comprise at least one or two amino acid residues on each of the N-terminal and C-terminal side of the lactylated lysine. Exemplary peptides of the present invention are shown in Table 1.

An isolated affinity reagent is also provided. The affinity reagent binds specifically to a lactylated lysine in a peptide, polypeptide or protein. This affinity reagent is also called a lysine lactylation specific affinity reagent. The peptide may be derived from a histone protein or a fragment thereof. The affinity reagent may be a protein, for example, an antibody. The lysine lactylation site may be any lysine lactylation site in any histone protein from any species. The lactylated lysine may be any lactylated lysine in any histone protein from any species. Examples of the lysine lactylation sites or lactylated lysine include those in Table 1, and homologous lysine sites in other corresponding eukaryotic histone proteins.

In some embodiments, the binding affinity of the affinity reagent for a lysine in a peptide, polypeptide or protein when the lysine is lactylated is at least about 10, 50, 100, 500, 1000 or 5000 times higher than that for the lysine in the peptide, polypeptide or protein when the lysine is not lactylated.

In other embodiments, the binding affinity of the affinity reagent for a lysine in a peptide, polypeptide or protein when the lysine is not lactylated is at least about 10, 50, 100, 500, 1000 or 5000 times higher than that for the lysine in the peptide, polypeptide or protein when the lysine is lactylated.

The affinity reagent may be a peptide, polypeptide or protein, which may be an antibody. Preferably, the peptide is a peptide comprising a lactylated lysine according to the present invention.

In some embodiments, the binding of the affinity reagent to a lactylated lysine in a peptide, polypeptide or protein depend on a surrounding peptide sequence of the lactylated lysine. The surrounding peptide sequence may include at least about 1, 2, 3, 4, 5, 6, 7, 8, 9, 10 or more residues on either or both of N-terminal and C-terminal sides of the lactylated lysine. For example, the binding may depend on at least one or two amino acid residues on the N-terminal side and/or C-terminal side of the lactylated lysine.

In other embodiments, the binding of the affinity reagent to a lactylated lysine in a peptide, polypeptide or protein does not depend on a surrounding peptide sequence of the lactylated lysine. For example, the affinity reagent may be an anti-lactylated lysine pan antibody.

A method for isolating an affinity reagent that binds specifically to a lactylated lysine in a peptide, polypeptide or protein is further provided.

Where the affinity reagent is a protein, the isolation method may comprise exposing a protein library (also known as a display library or a degenerated protein library) to a peptide comprising a lactylated lysine such that a protein from the protein library binds specifically to the lactylated lysine and forms a binding complex with the peptide, polypeptide or protein. The method further comprises isolating the protein from the binding complex. The isolated protein is the affinity agent.

The protein library may comprise many degenerated protein sequences, which may comprise two regions: one or more fixed peptide sequence regions and a plurality of degenerated amino acid sequences. The protein library may be a phage protein library, a yeast protein library, bacterial protein library, ribosome protein library, or other synthetic protein library comprising peptides having randomized amino acid sequences.

Where the affinity reagent is an antibody, the antibody may be isolated by different methods known in the art. For example, the isolation method may comprise immunizing a host with a peptide, polypeptide or protein comprising a lactylated lysine such that the host produces an antibody. The isolation method may further comprise isolating the antibody from the host. As a result, the isolated antibody is the affinity agent.

The host may be a mammal suitable for producing antibodies. For example, the host may be a mouse, rabbit, goat, Camelidae family animal (such as Lama and camel), or cartilaginous fishes. Depending on the host used, the generated antibody may contain either two chains (a heavy chain and a light chain) or one chain (or heavy chain-only antibody occurring in camelids) that is also called Nanobody.

The peptide, polypeptide or protein in the isolation method may have at least two, three, four or five amino acid residues on the N-terminal side and/or the C-terminal side of the lactylated lysine.

The peptide, polypeptide or protein in the isolation method may be derived from a histone protein or a fragment thereof comprising a lysine lactylation site, which may be lactylated or not, preferably lactylated.

Examples of peptides having a lactylated lysine may comprise one or more of the peptides in Table 1. Examples of the peptides not having a lactylated lysine may have an amino acid sequence identical to those in Table 1, except that the lysine lactylation site is not lactylated. The N-terminal or C-terminal end of any of these peptides may be extended by 1-20 residues.

The isolation method may further comprise purifying the antibody from antisera of the host. The method may further comprise utilizing spleen cells from the host to generate a monoclonal antibody. In some embodiments, the antibody specifically binds to a histone protein or fragment having a lysine lactylation site when the site is lactylated, but not when the site is not lactylated. In other embodiments, the antibody specifically binds to a histone protein or fragment having a lysine lactylation site when the site is not lactylated, but not when the site is lactylated.

The method may further comprise deducing the antibody sequences by high-performance liquid chromatography (HPLC)-mass spectrometry analysis of the isolated antibodies and followed by protein sequence database search against all the possible IgG protein sequences (derived from cDNA sequences) from bone marrow (or B cells) of the immunized host. The IgG cDNA sequences can be obtained from conventional DNA sequencing technologies from IgG cDNAs that are generated by RT-PCR using the known art. The derived heavy- and light-chain variable regions (VH and VL) can be further paired (in case the IgG is from a two-chain antibody from a host like mice or rabbit). Such a pairing is not necessary for those IgG derived from heavy chain-only antibody (or Nonabody) from Lama. The antibody can then be generated using the antibody sequence information using the known art.

A method for detecting a lactylated lysine in a protein or a fragment thereof is provided. The detection method comprises (a) contacting the protein or a fragment thereof with an affinity reagent of the present invention such that a binding complex of the protein or a fragment thereof and the affinity reagent is formed, and (b) detecting the binding complex. The protein may be a histone protein. The affinity reagent binds specifically to a lactylated lysine in a peptide of the present invention. The presence of the binding complex indicates the presence of a lactylated lysine in the protein or a fragment thereof. The binding complex may be detected by using various conventional methods in the art. The method may further comprise quantifying the lactylated lysine in the protein or a fragment thereof. The amount of the binding complex may indicate the amount of the lactylated lysine in the protein or its fragment.

For each detection method of the present invention, a kit is provided. The kit comprises an affinity reagent that binds specifically to a lactylated lysine in a peptide. The kit may further comprise an instruction for detecting a lactylated lysine in a protein or a fragment thereof using the affinity reagent according to the detection method of the present invention.

For each isolation method of the present invention, a kit is provided. The kit comprises a peptide comprising a lactylated lysine. The kit may further comprise an instruction for isolating an affinity reagent that binds specifically to the lactylated lysine in the peptide according to the isolation method of the present invention.

A fusion protein reporter is provided. The fusion protein reporter comprises a core flanked by a donor fluorescent moiety and an acceptor fluorescent moiety. The core includes a peptide, which comprises a lysine lactylation site and a lysine lactylation binding domain. The term "lysine lactylation binding domain" used herein refers to a region in a protein sequence capable of specific binding to the lysine lactylation site, which may be lactylated or not.

The fusion protein reporter of the present invention may be useful for determining protein lysine lactylation level in a sample or screening for an agent that regulates protein lysine lactylation by using the fluorescence resonance energy transfer (FRET). The FRET involves the transfer of photonic energy between fluorophores when in close proximity. Donor fluorescent moieties and acceptor fluorescent moieties suitable for FRET are known in the art. In the fusion protein reporter, the donor fluorescent moiety may be selected from the group consisting of cyan fluorescent protein (CFP), enhanced cyan fluorescent protein (ECFP), and A206K mutants thereof, and the acceptor fluorescent moiety may be selected from the group consisting of yellow fluorescent protein (YFP), enhanced yellow fluorescent protein (EYFP), Citrine, Venus, and A206K mutants thereof.

The peptide in the fusion protein reporter may comprise a peptide of the present invention. It may be derived from a histone protein or fragment comprising a lysine lactylation site, and the histone protein or fragment may be lactylated or not at the lysine lactylation site.

The lysine lactylation site may be located in the N-terminus, C-terminus or the core region of a histone protein. The N-terminus, C-terminus, and core regions of histone proteins (e.g., human or mouse H1.2, H2A, H2B, H3 or H4) are known in the art.

The fusion protein reporter may comprise one or more lysine lactylation binding domains. A lysine lactylation binding domain may be derived from a lysine lactylation specific affinity reagent of the present invention.

In some embodiments, the lysine lactylation site in the peptide is not lactylated, and the lysine lactylation binding domain specifically binds to the lysine lactylation site in the peptide when the site is lactylated, but not when the site is not lactylated.

In other embodiments, the lysine lactylation site in the peptide is lactylated, and the lysine lactylation binding domain specifically binds to the lysine lactylation site in the peptide when the peptide is not lysine lactylated, but not when the site is lactylated.

The lysine lactylation site may be conjugated to the lysine lactylation binding domain with a linker molecule. The linker molecule may be a peptide have any amino acid sequence, and may have about 1-50 amino acids, preferably 1-30 amino acids, more preferably 2-15. In some embodiments, the linker molecule may be -Gly-Gly-. The length and contents of a linker molecule may be adjusted to optimize potential fluorescence resonance energy transfer (FRET) between the donor fluorescent moiety and the acceptor fluorescent moiety when the lysine lactylation site in the fusion protein reporter is lactylated or not, and bound by the lysine lactylation binding domain.

The fusion protein reporter may further comprise a targeting polypeptide. The targeting polypeptide may be selected from the group consisting of a receptor ligand, a nuclear localization sequence (NLS), a nuclear export signal (NES), a plasma membrane targeting signal, a histone binding protein, and a nuclear protein.

A method for determining the level of protein lysine lactylation in a sample. The method comprises detecting a lactylated lysine in the sample. The method may comprise (a) contacting the sample with a fusion protein reporter of the present invention, and (b) comparing the level of fluorescence resonance energy transfer (FRET) between the donor fluorescent moiety and the acceptor fluorescent moiety after contacting with that before contacting. The level of FRET indicates the level of protein lysine lactylation in the sample. The level of FRET may be increased or decreased after contacting.

A method for determining the level of protein de-lysine-lactylation in a sample is also provided. The method comprises (a) contacting the sample with a fusion protein reporter of the present invention, and (b) comparing the level of fluorescence resonance energy transfer (FRET) between the donor fluorescent moiety and the acceptor fluorescent moiety after contacting with that before contacting. The level of FRET indicates the level of protein de-lysine-lactylation in the sample. The level of FRET may be increased or decreased after contacting.

For the determination method of the present invention, a sample may be a biological sample (e.g., bodily fluid or serum). The biological sample may comprise a cell, a tissue biopsy, or a clinical fluid. The biological sample may be obtained from a subject (e.g., a mouse, rat, or human). The subject is healthy. The subject may have suffered from or may be predisposed to a protein lysine lactylation or de-lysine-lactylation related disorder, which may be any disorder or disease linked to abnormal regulation of protein lysine lactylation or de-lysine-lactylation, respectively. Examples of such disorder or disease may include cancer, neurodegenerative diseases, aging, metabolic disorder, and dysgenesis.

The determination method of the present invention may further comprise comparing the FRET level in the sample with a control FRET level. The control FRET level may be the FRET level in a control sample obtained from a subject, who is healthy or has not suffered from or predisposed to a protein lysine lactylation related disorder. The FRET level in the sample may be higher or lower than the control FRET level.

The determination method of the present invention may further comprise adding an agent to the sample. In some embodiments, the agent is known to promote or inhibit protein lysine lactylation. In other embodiments, the agent is a screening candidate for a regulator of protein lysine lactylation. The screening candidate may be a compound or a biological molecule.

For each determination method of the present invention, a kit is provided. The kit comprises a fusion protein of the present invention. The kit may further comprise an instruction directing how to carry out the method.

A kit for isolating a peptide containing a lactylated lysine is also provided. The kit comprises an isolated lysine lactylation specific affinity reagent capable of binding specifically to a peptide comprising a lactylated lysine.

A method for treating or preventing a protein lysine lactylation related disease in a subject in need thereof is provided. The method comprises administering to the subject an effective amount of a composition comprising an agent that regulates protein lysine lactylation. The agent may be a screen candidate identified by a determination method of the present invention. The protein lysine lactylation may be histone lysine lactylation.

A method for treating or preventing a protein or de-lysine-lactylation related disease in a subject in need thereof is provided. The method comprises administering to the subject an effective amount of a composition comprising an agent that regulates protein de-lysine-lactylation. The agent may be a screen candidate identified by a determination method of the present invention. The protein de-lysine-lactylation may be histone de-lysine-lactylation.

The term "about" as used herein when referring to a measurable value such as an amount, a percentage, and the like, is meant to encompass variations of ±20% or ±10%, more preferably ±5%, even more preferably 1%, and still more preferably ±0.1% from the specified value, as such variations are appropriate.

Example 1. Metabolic Regulation of Gene Expression by Histone Lactylation

Inspired by the discovery of various histone acylations derived from cellular metabolites, we predicted and identified lysine lactylation (Kla) as a new type of histone mark that can be stimulated by lactate (illustrated in FIG. 1a). Initial evidence for histone Kla came from the observation of a mass shift of 72.021 Daltons on lysine residues in three proteolytic peptides that were detected in high performance liquid chromatography (HPLC)-tandem mass spectrometric (MS/MS) analysis of tryptically digested core histones from MCF-7 cells (FIG. 1b). This mass shift is the same as that caused by addition of a lactyl group to the E amino group of a lysine residue.

To validate the existence of lysine lactylation in histones, we used four orthogonal methods. In the first two methods, we used HPLC-MS/MS to compare a synthetic peptide and its in vivo-derived counterpart to determine whether the two versions of the peptide have the same chemical properties in terms of chromatographic elution in HPLC and fragmentation pattern in MS/MS. To this end, we generated three histone peptides bearing Kla modifications: H3K23-QLAT-KiaAAR (SEQ ID NO: 85), H2BK5-PELAKiaSAPAPK (SEQ ID NO: 86), and H4K8-GGKiaGLGK (SEQ ID NO: 87). Each pair of peptides co-eluted in HPLC and had comparable MS/MS spectra (FIG. 1b). To further confirm the modification, we developed a pan anti-Kla antibody. Immunoblots using the pan anti-Kla antibody confirmed the presence of histone Kla and showed that histone Kla levels were elevated in a dose-dependent fashion in response to exogenous L-lactate. Subsequent MS analyses identified 26 and 16 histone Kla sites from human MCF-7 cells and mouse bone marrow-derived macrophages (BMDMs), respectively (FIG. 1c). Finally, metabolic labeling experiments using isotopic sodium L-lactate ($^{13}C_3$) followed by MS/MS analysis demonstrated that lysine lactylation can be derived from lactate. Together, these experiments demonstrate that histone Kla is an in vivo protein post-translational modification derived from lactate.

Figure 2:
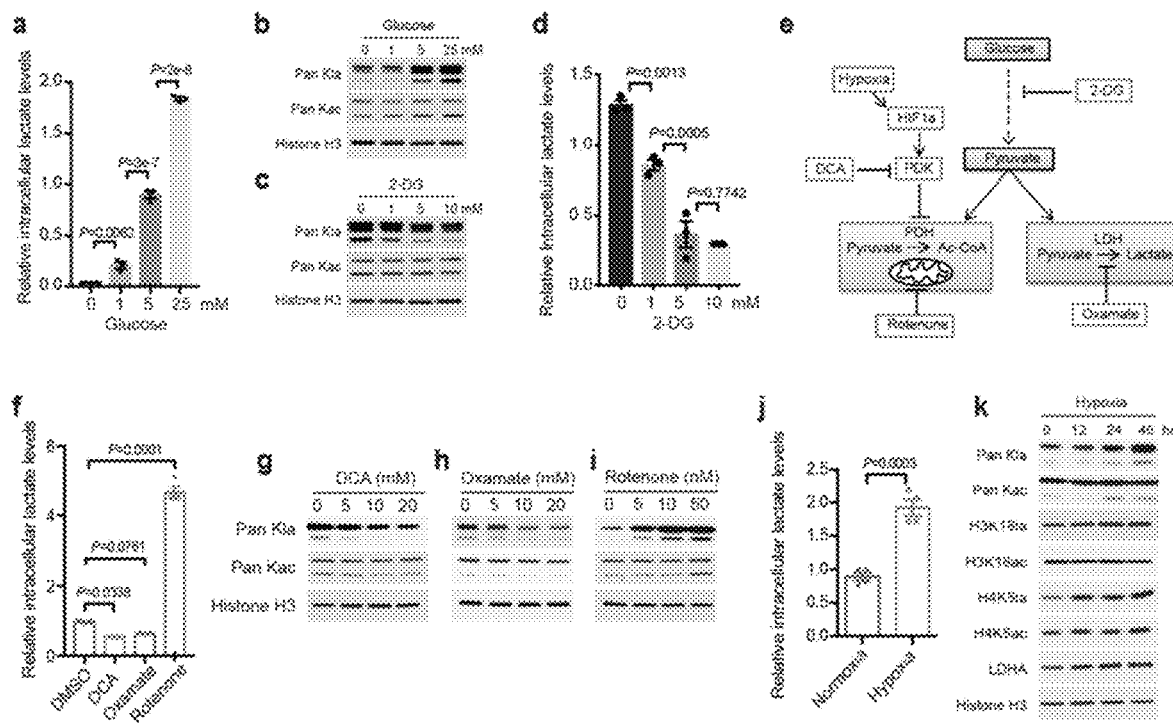
FIG. 2 shows regulation of histone Kla by lactate. Intracellular lactate (a and d) and histone Kla levels (b and c) were measured from MCF-7 cells cultured in different glucose concentrations or different 2-DG concentrations in the presence of 25 mM glucose for 24 hours. Lactate was measured by a lactate colorimetric kit; n=3 biological replicates; statistical significance was determined using one-way ANOVA followed by Sidak's multiple comparisons test. Immunoblots was carried out using acid-extracted histone samples. The pan anti-Kla and anti-Kac immunoblots indicate molecular weights between 10 kD and 15 kD. e, Regulation of glycolysis and lactate production by diverse metabolic modulators. f, Intracellular lactate levels were measured in MCF-7 cells treated with indicated glycolysis modulators for 24 hours. N=3 biological replicates; statistical significance was determined using one-way ANOVA followed by Dunnett's multiple comparisons test. g-i, Immunoblots of acid extracted histones (Rotenone and DCA) or whole cell lysates (Oxamate) from MCF-7 cells in response to different glycolysis modulators. j, Intracellular lactate levels were measured in MCF-7 cells in response to hypoxia. N=4 biological replicates; statistical significance was determined using unpaired t test (Two-tailed). k, Immunoblots of acid extracted histones from MCF-7 cells under hypoxia (1% oxygen) for indicated time points. a, d, f, j, Graphs show mean with s.e.m. b, c, g, h, i, k, Data represent three independent experiments.

Given that extracellular lactate can stimulate histone Kla, we hypothesized that modulation of intracellular lactate production would also impact histone Kla levels. We exposed MCF-7 and other cell lines to various concentrations of glucose, the major source of intracellular lactate. Both lactate production and histone Kla levels were induced by glucose in a dose-dependent manner (FIG. 2a, b). Conversely, 2-deoxy-D-glucose (2-DG), a non-metabolizable glucose analog, decreased both lactate production and histone Kla levels (FIG. 2c, d). Furthermore, metabolic labeling experiments using isotopic glucose (U-$^{13}C_6$) followed by MS/MS analysis demonstrated that lysine lactylation is endogenously derived from glucose. Quantitative proteomics analysis across a diverse set of histone sites demonstrated that histone Kla and Kac have different kinetics of $^{13}C$ glucose incorporation in MCF-7 cells. $^{13}C$ labeled histone Kac reached a steady state at 6 h, similar to the observation in HCT116 cells by Liu et al (Cell 175, 502-513 e513, doi:10.1016/j.cell.2018.08.040 (2018). In contrast, histone Kla increased over a 24 h time course. Immunoblotting results corroborated the MS/MS data in MCF-7 as well as other cell lines.

Lactate production is determined by the balance between glycolysis and mitochondrial metabolism. We tested whether the activities of enzymes in these two pathways can modulate lactate levels that in turn regulates histone Kla (illustrated in FIG. 2e). Sodium dichloroacetate (DCA) and oxamate were used to inhibit lactate production by modulating activities of pyruvate dehydrogenase (PDH) and lactate dehydrogenase (LDH), respectively. As anticipated, intracellular lactate levels were decreased by these two compounds (FIG. 2f) and histone Kla levels were lowered (FIG. 2g, h). Conversely, rotenone, an inhibitor of the mitochondrial respiratory chain complex I that drives cells towards glycolysis increased both intracellular lactate and histone Kla levels (FIG. 2f, i). Quantification of histone Kla and Kac marks by Stable Isotope Labeling with Amino Acids in Cell Culture (SILAC) and MS/MS analysis corroborated the immunoblot data from DCA- and Rotenone-treated MCF-7 cells. Furthermore, U-$^{13}C_6$ glucose labeling experiments showed that the incorporation of $^{13}C$ into histone Kla but not Kac was decreased by DCA. Together, these observations demonstrate that endogenous lactate production is a key determinant of histone Kla levels.

Elevated glycolysis and lactate production are coupled with diverse cellular processes. To investigate whether histone Kla is regulated by glycolysis under physiological conditions, we chose two model systems: hypoxia and M1 macrophage polarization. In response to hypoxia, cells reprogram their metabolism by inhibiting oxidative phosphorylation and enhancing glycolysis, stimulating the production of lactate. Hypoxia induced intracellular lactate production and increased histone Kla but not Kac levels in MCF-7 cells (FIG. 2j, k). SILAC-based mass spectrometric quantification of histone Kla and Kac confirmed the immunoblotting data. Similar results were obtained in HeLa and RAW264.7 cells. Furthermore, we found that the induction of lactate production and histone Kla by hypoxia were attenuated by an LDH inhibitor (Oxamate) or a PDK1 inhibitor (DCA). Deleting both LDHA and LDHB fully suppressed lactate production and histone Kla in HepG2 cells under normoxic conditions. Due to poor cell viability, hypoxic conditions could not be tested.

Emerging evidence shows that lactate has regulatory functions in both innate and adaptive immune cells and induces dramatic changes in gene expression, suggesting that lactate is not simply a "waste product" of glycolysis. Pro-inflammatory M1 macrophages undergo metabolic reprogramming toward aerobic glycolysis, resulting in lactate production, whereas anti-inflammatory M2 macrophages trigger a metabolic program of increased oxidative phosphorylation and fatty acid oxidation. Our discovery of histone Kla marks and their dynamics therefore suggests a role in regulating gene expression during M1 macrophage polarization.

Figure 3:
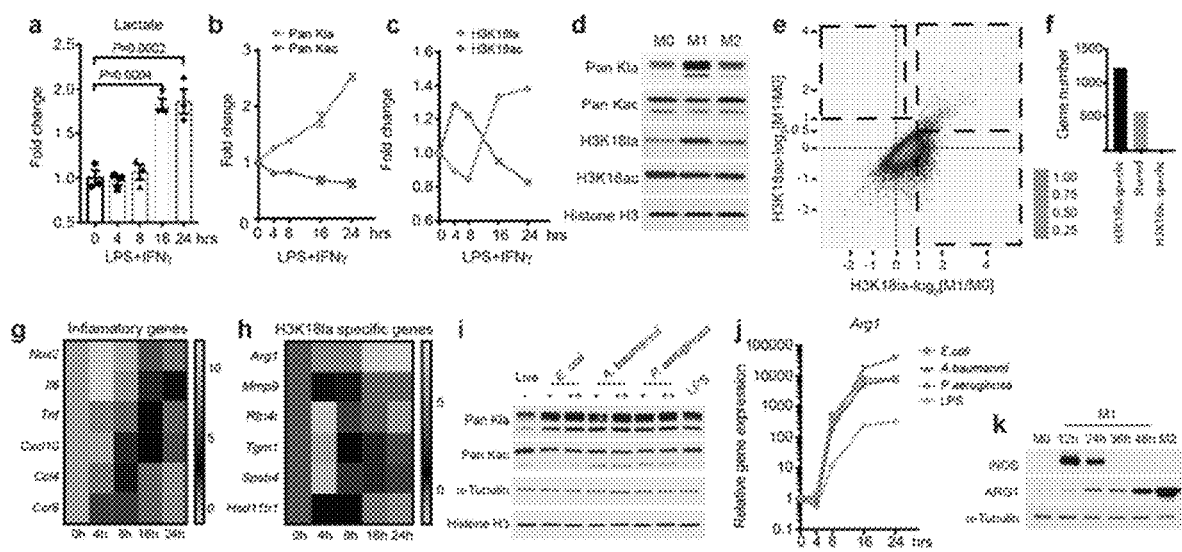
FIG. 3 shows elevated histone Kla during M1 macrophage polarization is associated with M2-like gene activation. a-c, Bone marrow-derived macrophages (BMDMs) were activated with LPS+IFNγ. Intracellular lactate (a) was measured using a lactate colorimetric kit. N=3 biological replicates; statistical significance was determined using one-way ANOVA followed by Dunnett's multiple comparisons test. Histone acylations were analyzed by immunoblots using whole cell lysates (b, c). ImageJ was used for quantification; n=3 technical replicates. Data represent two independent experiments. d, BMDM cells were stimulated with PBS (M0), LPS+IFNγ (M1), and interleukin-4 (M2) for 24 hours, respectively. Acid-extracted histones were used for immunoblots. e, f, Scatter plot (e) and bar plot (f) showing genes with promoters marked by exclusively elevated H3K18la (H3K18la-$\log_2$[M1/M0]≥1 and H3K18ac-$\log_2$[M1/M0]≤0.5, H3K18la-specific), elevated in both H3K18la and H3K18ac (H3K18la-$\log_2$[M1/M0]≥1 and H3K18ac-$\log_2$[M1/M0]≥0.5, shared), or exclusively elevated H3K18ac (H3K18ac-$\log_2$[M1/M0]≥1 and H3K18la-$\log_2$[M1/M0]≤0.5, H3K18ac-specific). g, h, Heat maps showing gene expression kinetics (using Reads Per Kilobase of transcript per Million mapped reads (RPKM) values from RNA-seq) of exemplar inflammatory genes (g) and H3K18la-specific genes (h). The color key represents log 2 transformed fold change relative to gene expression at 0 h. N=4 biological replicates. i, j, BMDM cells were infected with indicated Gram-negative bacteria or LPS, respectively. Histone Kla levels were measured by immunoblots (i) at 24 h after bacterial challenge. "+" indicates lower dose and "++" indicates higher dose. Gene expression were analyzed by RT-qPCR (j) at indicated time points post bacterial challenge. N=3 biological replicates. k, Protein levels of iNOS and ARG1 were analyzed by immunoblots from BMDMs activated by the indicated stimuli. a, b, c, j, Graphs show mean with s.e.m. d, i, k, Data represent three independent experiments.

To test this hypothesis, we examined the dynamics of lactate production and histone Kla marks during M1 macrophage polarization following treatment of BMDMs with lipopolysaccharide (LPS) and interferon-γ (IFNγ). We observed increased intracellular lactate levels 16 to 24 hours after M1 activation (FIG. 3a), which were well correlated with increased histone Kla levels (FIG. 3b, c). In contrast, histone Kac levels were decreased at these time points (FIG. 3b, c). This differential pattern was confirmed by U-$^{13}C_6$ glucose labeling experiments, which showed that $^{13}C$ labeled histone Kac peaked 3 hr after labeling and declined to a steady state, while histone Kla increased over the 24 h time course. In addition, GNE-140, an LDHA specific inhibitor reduced $^{13}C$ incorporation into histone Kla, but not Kac. The increase of histone Kla during M1 polarization is intrinsic and not due to paracrine effects, because replenishing cells with fresh media every 4 hours did not affect Kla levels. Increases in lactate production and histone Kla are also specific to M1 macrophages because they were not observed in M2-polarized BMDMs (FIG. 3d), which are more reliant on fatty acid oxidation.

Histone modifications play an important role in the regulation of gene expression. To investigate histone Kla-associated genes 24 hours post-M1 polarization of macrophages, we performed RNA-seq and paired ChIP-seq using anti-H3K18la or anti-H3K18ac antibodies, whose specificities were validated by dot blots, ChIP-qPCR assays and immunoblots.

Our ChIP-seq data showed that H3K18la and H3K18ac were both enriched in promoter regions (±2 kb around transcriptional start sites) and were indicative of steady-state mRNA levels. In addition, elevated H3K18la (2-fold increase) marked more genes than decreased H3K18la (2-fold decrease), while the converse was true for the H3K18ac modification (FIG. 3e). Moreover, the majority of genes marked by elevated H3K18la were specific, since 68% of these genes (1223/1787) did not display significantly elevated H3K18ac (FIG. 3e, f). In contrast, no H3K18ac-specific genes were identified (FIG. 3e, f).

To study correlations between H3K18la marks and gene expression, we performed RNA-seq 0, 4, 8, 16, and 24 hours after LPS/IFNγ challenge. As expected, inflammatory response genes (e.g., Nos2) were induced as early as 4 hours following LPS/IFNγ challenge, and their expression levels steadily declined at later time points (FIG. 3g). Interestingly, the 1223 genes specifically marked by elevated H3K18la were more likely to be activated or reactivated at later time points (16 or 24 hours) during M1 polarization (FIG. 3h), which correlated well with the induction of intracellular lactate and histone Kla levels at these later time points (FIG. 3a-c). Gene Ontology (GO) analysis revealed that these H3K18la-specific genes were enriched in biological pathways independent of inflammation. One of these enriched pathways was wound healing (e.g., Arg1), which has been associated with the M2-like phenotype (FIG. 3h). To corroborate these findings with more physiologically relevant stimuli, we treated BMDMs (M0) with live or dead gram-negative bacteria (E. coli, A. baumannii, and P. aeruginosa) to stimulate M1 polarization. Similar to LPS, bacteria induced lactate production and global histone Kla but not histone Kac levels (FIG. 3i), and kinetics of early cytokine and late Arg1 expression were maintained (FIG. 3j).

Arginine metabolism is a key catabolic and anabolic process that is regulated during macrophage polarization. M1 macrophages are thought to have low ARG1 and to metabolize arginine to produce nitric oxide through nitric oxide synthase to kill pathogens, while M2 macrophages have high ARG1 which produces ornithine to facilitate wound healing. Consistent with their RNA dynamics, ARG1 protein levels and activity were significantly increased 24-48 hours post-M1 polarization, while NOS2 protein levels and function peaked 12 hours post-M1 polarization and declined at later time points (FIG. 3k). Collectively, these findings suggest that induction of lactate during M1 activation might promote a late-phase switch to a more homeostatic phenotype, which shares some similarity with the M2-like phenotype. Indeed, previous studies showed that treating BMDMs with tumor cell-derived lactate drives an M2-like phenotype characteristic of tumor-associated macrophages (TAMs). Using murine cancer models, we observed a positive correlation between Arg1 expression and histone Kla levels, but not histone Kac levels in TAMs isolated from B16F10 melanoma and LLC1 lung tumors.

Figure 4:
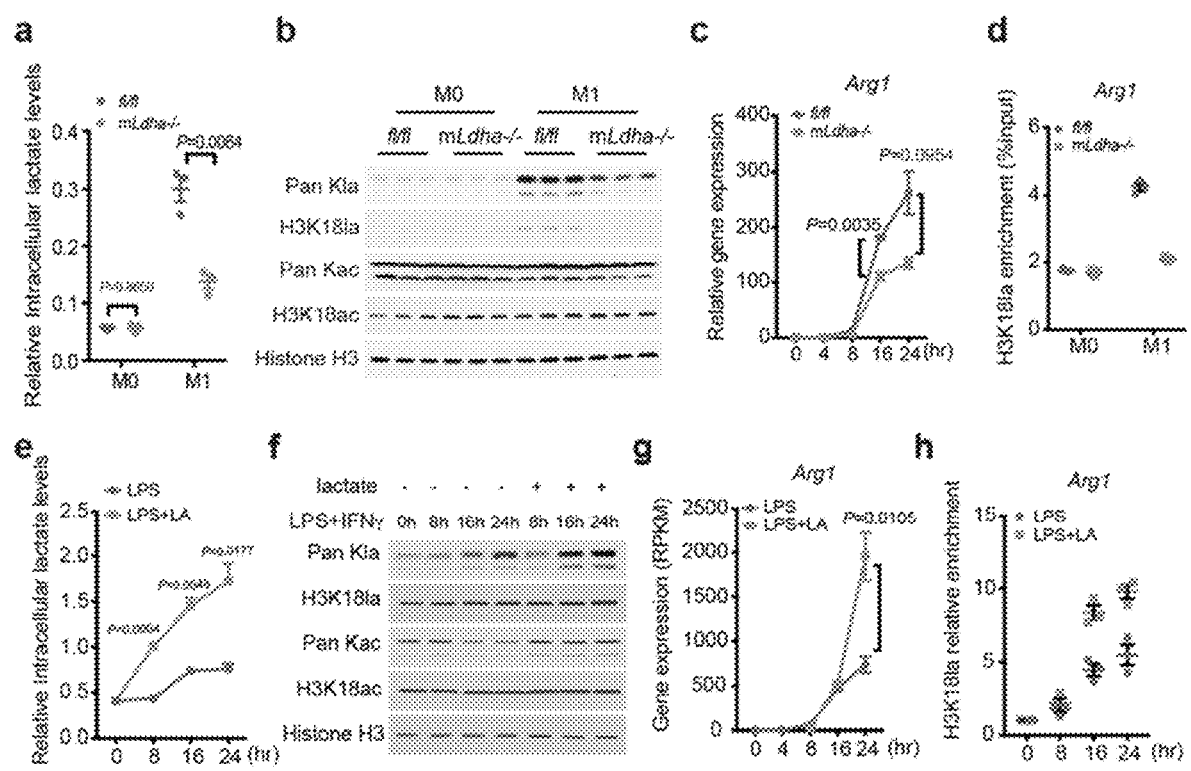
FIG. 4 shows activation of M2-like gene expression by lactate through histone Kla. a-d, Decreased lactate production in LDHA deficient (myeloid specific Ldha$^{-/-}$) BMDM cells resulted in lowered histone Kla levels and Arg1 expression during M1 polarization. Intracellular lactate levels were measured using a lactate colorimetric kit (a) and global histone Kla levels were measured by immunoblots (b) 24 h-post M1 polarization. c, Gene expression were analyzed by RT-qPCR at indicated time points after M1 polarization. a-c, N=3 biological replicates. d, H3K18la occupancy was analyzed by ChIP-qPCR 24 h-post M1 polarization. Data represent three technical replicates from pooled samples. e-h, Exogeneous lactic acid (25 mM) was added to BMDM cells 4 h post-M1 polarization (LPS+IFNγ), and cells were collected at indicated time points post-M1 polarization for intracellular lactate measurement (e), histone Kla immunoblot analysis (f), gene expression analysis (g) and H3K18la occupancy analysis by ChIP-qPCR (h). e, N=3 biological replicates, f, Data represent three independent experiments. g, RPKM: Reads Per Kilobase of transcript per Million mapped reads (RPKM). N=4 biological replicates. h, Data represent three technical replicates from pooled samples. a, c, d, e, g, h, Graphs show mean with s.e.m; statistical significance was determined using Multiple t tests corrected using Holm-Sidak method (a, c, e, g).

Changes in gene expression during M1 polarization are caused by complex signaling cascades induced by LPS/IFNγ, including the induction of lactate and histone Kla. To substantiate the role of lactate and histone Kla in the regulation of gene expression, we manipulated levels of lactate during M1 polarization and examined its effect on expression of Arg1, a M2-like gene. We first lowered lactate levels by deleting Ldha (LysM-Cre$^{+/-}$Ldha$^{fl/fl}$). Lactate production and global histone Kla levels were both decreased in LDHA-deficient macrophages during M1 polarization (FIG. 4a, b). Although deleting Ldha in macrophages did not alter proinflammatory cytokine expression, it attenuated Arg1 and decreased histone Kla marks at the Arg1 promoter (FIG. 4c, d). Similar findings were obtained when macrophages were M1 polarized in the presence of the glycolysis inhibitors (2-DG, DCA and GNE-140). Next, we elevated lactate levels by treating M1 macrophages with exogenous lactate. Exogenous lactate increased intracellular lactate (FIG. 4e) and histone Kla levels (FIG. 4f), and induced Arg1 expression (FIG. 4g) and Kla levels at the Arg1 promoter (FIG. 4h). In contrast, exogenous lactate did not affect early proinflammatory gene expression. In addition, exogenous lactate enhanced expression of other M2-like genes, such as Vegfa during M1 polarization. Thus, this data confirmed the positive role of lactate and histone Kla in driving expression of M2-like genes during M1 macrophage polarization.

Our observed correlations between lactate, H3K18la, and M2-like gene expression does not necessarily imply that the histone Kla mark was a causative factor. Previous studies showed that exogenous lactate can alter Arg1 and Vegfa expression in unstimulated (M0) macrophages through HIF1a. However, HIF1a is unlikely to be important for regulating Arg1 and Vegfa during M1 polarization as HIF1a protein was induced at early time points and HIF1a bound to promoters of glycolytic genes but not Arg1 and Vegfa.

To examine whether histone Kla plays a direct role in transcriptional regulation, we took advantage of a cell-free, recombinant chromatin-templated histone modification and transcription assay that was used previously to demonstrate direct transcriptional activation by p53- and p300-dependent histone Kac. This assay, in which acetyl-CoA was replaced by L-lactyl-CoA (validated by HPLC and MS, demonstrated robust p53-dependent, p300-mediated H3 and H4 lactylation and a corresponding effect on transcription. The effects paralleled those observed for acetyl-CoA dependent-histone acetylation and transcription. To confirm that transcription was directly mediated by lactylation of histones, rather than other proteins in the nuclear extract, recombinant chromatin was reconstituted with core histones bearing lysine (K) to arginine (R) mutations in histone tails. Compared to wild type histones, the H3 and H4 mutations, but not the H2A or H2B mutations, eliminated p300- and p53-dependent transcription. Taken together, these findings suggest that histone lactylation, like histone acetylation, can directly promote gene transcription under the described conditions. To examine the potential activity of p300 as a histone Kla writer in cells, we over-expressed p300 in HEK293T cells and observed a modest increase in histone Kla levels. In contrast, p300 deletion in HCT116 and HEK293T cells decreased histone Kla levels. Although we cannot exclude an indirect effect by p300 in these cells, together with the in vitro enzymatic results, these data suggest that p300 is a potential histone Kla writer protein.

In response to bacterial infection, macrophages must react rapidly with a substantial pro-inflammatory burst to help kill bacteria and recruit additional immune cells to the infection site. During this process, macrophages switch to aerobic glycolysis, which is thought to support pro-inflammatory cytokine expression during M1 activation and produce the Warburg effect. Over time, this metabolic switch also increases intracellular lactate, which we show stimulates histone lysine lactylation 16-24 hours after exposure to M1-polarizing stimuli. Histone lactylation is not required for the induction or suppression of pro-inflammatory genes. Instead, it serves as a mechanism to initiate expression of homeostatic genes that have been traditionally associated with M2-like macrophages. Our studies support a model wherein the switch to aerobic glycolysis that occurs during M1 polarization starts a "lactate timer" that uses an epigenetic mechanism to induce M2-like characteristics in the late phase, perhaps to assist with repairing collateral damage incurred by the host during infection.

High levels of lactate (e.g., 40 mM in certain type of tumor tissue) is also associated with major hallmarks of cancer and other diseases. Given that the Kla modification can be stimulated by lactate and contribute to gene expression, the Kla modification will likely fill an important knowledge gap in our understanding of diverse physiopathology (e.g., infection, cancer) with which lactate is intimately associated.

Methods

Materials.

Pan anti-Kac (PTM-101), pan anti-Kla (PTM-1401), anti-H3K18la (PTM-1406), anti-H4K51a (PTM-1407), and anti-H4K81a (PTM-1405) antibodies were generated by PTM Bio Inc. (Chicago, IL); anti-histone H3 (ab12079), anti-H3K18ac (ab1191) and anti-H3K27ac (ab4729) antibodies were purchased from Abcam (Cambridge, MA); Drosophila spike-in antibody (61686) and spike-in chromatin (53083) were obtained from Active Motif (Carlsbad, CA); anti-LDHA (2012S) antibody was from Cell Signaling Technology, Inc (Danvers, MA); anti-☐-Tubulin (05-829) and anti-LDHB (ABC927) antibodies were from Millipore Sigma (Burlington, MA); anti-HIF-1a (NB100-105) antibody was from Novus Biologicals (Littleton, CO); anti-iNOS (GTX130246) and anti-Arg1(GTX109242) antibodies were purchased from GeneTex (Irvine, CA); anti-p300 (sc-584) was from Santa Cruz Biotechnology, Inc (Dallas, TX); anti-CD11b Monoclonal Antibody (M1/70), PE-Cyanine7 (25-0112-82) and anti-F4/80 Monoclonal Antibody (BM8), APC (17-4801-82) were from ThermoFisher Scientific (Waltham, MA); lipopolysaccharides from *Escherichia coli* O111:B4 (L4391), sodium L-lactate (71718), L-(+)-lactic acid (L6402), sodium dichloroacetate (347795), Cobalt(II) chloride hexahydrate (C8661), rotenone (R8875), and acetyl coenzyme A (A2056) were purchased from Sigma-Aldrich (St. Louis, MO); sodium L-lactate ($^{13}C_3$, 98%) (CLM-1579-PK) and D-glucose (U-$^{13}C_6$, 99%) (CLM-1396-1) were purchased from Cambridge Isotope Laboratories (Andover, MA). Recombinant mouse IFN-γ protein (485-MI-100) was from R&D Systems (Minneapolis, MN); mouse interleukin-4 (130-097-760) was from Miltenyi Biotec (Bergisch Gladbach, Germany); modified sequencing-grade trypsin was from Promega (Madison, WI); lactate colorimetric assay kit II (K627-100), arginase activity colorimetric assay kit (K755-100), and nitric oxide synthase (NOS) activity assay kit (K205-100) were purchased from Biovision, Inc (Milpitas, CA).

Cell Culture.

MCF-7, MDA-MB-231, HeLa, A549, HepG2, MEF, and RAW 264.7 cells were obtained from the American Type Culture Collection and cultured in Dulbecco's modified Eagle's medium supplemented with 10% FBS and 1% GlutaMAX (GIBCO, Gaithersburg, MD). Cells were routinely tested for *mycoplasma* contamination (MP0035, Sigma-Aldrich, St. Louis, MO), and only negative cells were used in experiments. No specific cell line authentication was performed. For growth under hypoxic conditions, cells were grown in a specialized, humidified chamber equilibrated with 1% oxygen/94% nitrogen/5% carbon dioxide for the indicated time.

Mouse Experiments.

All animal use and experiments performed were approved by Institutional Animal Care and Use Committee (ACUP #72209) at the University of Chicago. Ldha$^{fl/fl}$ mice (Jackson laboratory, 030112) and LysMcre mice (Jackson laboratory, 004781) were used to generate LysMcre$^{+/-}$Ldha$^{fl/fl}$ and littermate control LysMcre$^{-/-}$ Ldha$^{fl/fl}$ mice. The following primers were used for genotyping: Ldha forward: CTGAGCACACCCATGTGAGA (SEQ ID NO: 88) and Ldha reverse: AGCAACACTCCAAGTCAGGA (SEQ ID NO: 89). LysMcre: CCCAGAAATGCCAGATTACG (SEQ ID NO: 90), LysM Common: CTTGGGCTGCCAGAATTCTC (SEQ ID NO: 91) and LysM WT: TTACAGTCGGCCAGGCTGAC (SEQ ID NO: 92). Macrophages were derived from bone marrow of 8-week male C57BL/6 mice following the published procedure. To induce an M1 or M2 phenotype, BMDM cells were stimulated with 5 ng/ml of LPS and 12 ng/ml of IFNγ or 20 ng/ml of interleukin 4, for 24 hours or the indicated time. To infect BMDM cells with bacteria, overnight cultures of *E. coli, A. baumannii,* or *P. aeruginosa* were diluted in RPMI-1640 and added to BMDM cells in 6-well plates at 2 and 20 multiplicity of infection. A control plate was either infected with paraformaldehyde-killed bacteria or treated with 5 ng/mL lipopolysaccharide (LPS) in the absence of bacteria. The plates were centrifuged at 2170 rpm for 30 min to promote infection, followed by a 30 min incubation in a humidified incubator at 37° C. under 5% $CO_2$. To kill extracellular bacteria, the medium overlying the confluent cell monolayer was replaced with fresh media containing gentamicin at 100 μg/mL and the plates were further incubated for 1 h. Following incubation, media were removed from infected cells and replaced with fresh media containing 25 μg/mL of gentamicin. For consistency, LPS-treated cells and cells infected with dead bacteria were also treated with gentamicin. Cells were cultured for 24 h before lysis. Allocation of BMDM cells into different treated groups were randomized and not blinded.

Tumor Inoculation and Tumor-Associated Macrophages (TAMs) Isolation.

LLC1 cells ($0.5 \times 10^6$) or B16F10 cells ($1 \times 10^6$) were injected into 7 weeks old C57BL/6 mice (The Jackson Laboratory). Once tumors reached ~600 mm³, mice were sacrificed for tumor isolation. Tumors were digested with Type 4 Collagenase (Worthington, 3 mg/mL) and hyaluronidases (Sigma, 1.5 mg/mL) in 1% BSA/PBS at 37° C. with shaking at 200 rpm for 30 min. The digested tumor was then filtered through a 70-um cell strainer, followed by RBC lysis step and passing through another 40-um strainer. Cells were resuspended into isolation buffer (0.1% BSA/PBS, 2 mM EDTA), layered onto Ficoll-Paque™ PLUS (GE Healthcare), and centrifuged at 450 g for 30 mins without break. Mononuclear immune cells were obtained by taking out the middle white layer. TAMs were then isolated using CD11b Microbeads (Mitenyi Biotec) as company instructed. TAMs' purity was confirmed by flow cytometry using CD11b and F4/80 antibody. Data were quantified by FlowJo v.10.4.1.

Peptide Immunoprecipitation.

Histones from human MCF-7 or mouse BMDM cells were extracted using a standard acid extraction protocol (Shechter et al., *Nat Protoc* 2, 1445-1457, doi:10.1038/nprot.2007.202 (2007)), and subjected to trypsin digestion as per the manufacturer's instructions. Pan anti-Kla or pan anti-Kac antibodies were first conjugated to nProtein A Sepharose beads (GE Healthcare BioSciences, Pittsburgh, PA) and then incubated with tryptically digested histone peptides with gentle agitation overnight at 4° C. The beads were then washed three times with NETN buffer (50 mM Tris-Cl pH 8.0, 100 mM NaCl, 1 mM EDTA, 0.5% NP-40), two times with ETN buffer (50 mM Tris-Cl pH 8.0, 100 mM NaCl, 1 mM EDTA) and once with water. Peptides were eluted from the beads with 0.1% TFA and dried in a SpeedVac system (Thermo Fisher Scientific, Waltham, MA).

HPLC/MS/MS Analysis.

The peptide samples were loaded onto a home-made capillary column (10 cm length×75 mm ID, 3 µm particle size, Dr. Maisch GmbH, Ammerbuch, Germany) connected to an EASY-nLC 1000 system (Thermo Fisher Scientific, Waltham, MA). Peptides were separated and eluted with a gradient of 2% to 90% HPLC buffer B (0.1% formic acid in acetonitrile, v/v) in buffer A (0.1% formic acid in water, v/v) at a flow rate of 200 nL/min over 60 min (34 min for coelution studies). The eluted peptides were then ionized and analyzed by a Q-Exactive mass spectrometer (Thermo Fisher Scientific, Waltham, MA). Full MS was acquired in the Orbitrap mass analyzer over the range m/z 300-1400 with a resolution of 70,000 at m/z 200. The 12 most intense ions with charge ≥2 were fragmented with normalized collision energy of 27 and tandem mass spectra were acquired with a mass resolution of 17500 at m/z 200.

Isotopic Labeling Experiments.

MCF-7 cells were cultured in DMEM high glucose media plus 10% FBS. To be labeled by isotopic lactate, cells were treated with 10 mM of $^{13}C_3$ sodium L-lactate for 24 hours. To be labeled by isotopic glucose, cells were switched to DMEM No-Glucose media (Gibco) for 24 hours, followed by supplementation with 25 mM of U-$^{13}C_6$ D-glucose and continued culturing for three passages. Histones were extracted, digested with trypsin, immunoprecipitated using a pan anti-Kla antibody, and analyzed by HPLC/MS/MS as described above.

SILAC-Based Quantification.

MCF-7 cells were cultured in either "heavy" (L-Lysine-$^{13}C_6$, $^{15}N_2$) or "light" (L-Lysine-$^{12}C_6$, $^{14}N_2$) DMEM, supplemented with 10% dialyzed FBS (Serum Source International Inc, Charlotte, North Carolina.), for more than six passages, to achieve more than 99% labeling efficiency. "Heavy" labeled and "light" labeled cells were mixed in a 1:1 ratio. Histones were extracted, digested with trypsin, immunoprecipitated using a pan anti-Kla antibody, and analyzed by HPLC/MS/MS as described above. Quantification was analyzed by Maxquant[20]. Ratio H/L derived from Maxquant was then normalized by protein abundance.

Synthesis of L-Lactyl-CoA.

L-Lactic acid (90 mg, 1 mmol) was dissolved in 5 mL of freshly distilled $CH_2Cl_2$. To this solution was added N-hydroxysuccinimide (115 mg, 1 mmol), the reaction mixture was sonicated to obtain a clear solution. Then N,N'-Dicyclohexylcarbodiimide (DCC, 227 mg, 1.1 mmol) was added in one portion. A white precipitate formed upon addition. The reaction mixture was stirred at r.t. overnight. Then the white precipitate was filtered and washed with $CH_3CN$. The resulting organic solvent was evaporated by vacuum to afford crude product L-lactyl-NHS (170 mg, 91% yield), which was used in the next step without further purification. 0.0065 mmol of CoA hydrate (5 mg) was dissolved in 1.5 mL of 0.5 M $NaHCO_3$ (pH 8.0) and cooled down on ice bath. Then L-lactyl-NHS (2.5 mg, 0.013 mmol) in 0.5 mL of $CH_3CN$/Acetone (1:1 v/v) was added dropwise to the CoA solution. The reaction solution was stirred at 4° C. overnight and then quenched by adjusting pH to 4.0 with 1.0 M HCl. The reaction mixture was then subjected to RP-HPLC purification with gradient 5-45% Buffer A in Buffer B over 30 min at flow rate 5 mL/min; UV detection wavelength was fixed at 214 and 254 nm (HPLC buffer A: 0.05% TFA in water; HPLC buffer B: 0.05% TFA in acetonitrile). The fractions were collected and lyophilized after flash-freeze with liquid nitrogen. m=2 mg, yield 38% $^1$H NMR (400 MHz, Deuterium Oxide) δ 8.57 (s, 1H), 8.33 (s, 1H), 6.12 (d, J=5.7 Hz, 1H), 4.49 (s, 1H), 4.29-4.24 (m, 1H), 4.14 (s, 2H), 3.93 (s, 1H), 3.75 (d, J=8.6 Hz, 1H), 3.48 (d, J=7.6 Hz, 1H), 3.35 (t, J=6.4 Hz, 2H), 3.22 (d, J=5.2 Hz, 3H), 2.89 (q, J=6.2 Hz, 2H), 2.32 (t, J=6.4 Hz, 2H), 1.23 (d, J=6.9 Hz, 3H), 0.83 (s, 3H), 0.70 (s, 3H). MALDI m/z calcd. for $C_{24}H_{41}N_7O_{18}P_3S$+[M+H]+: 840.1, found 839.6.

In Vitro Chromatin Template-Based Histone Modification and Transcription Assays.

Purification of recombinant proteins and chromatin assembly were performed as previously described (Tang et al., *Cell* 154, 297-310, doi:10.1016/j.cell.2013.06.027 (2013)). The chromatin-templated histone modification and transcription assays were as described previously (Tang et al., *Cell* 154, 297-310, doi:10.1016/j.cell.2013.06.027 (2013)), except that lactyl-CoA was used in place of acetyl-CoA and [α-32P] CTP was used in place of [α-32P]-UTP. The H3KR, H4KR, H2AKR, and H2BKR histone mutants were the same as previously described (Tang et al., *Cell* 154, 297-310, doi:10.1016/j.cell.2013.06.027 (2013)). Histone modifications were monitored by immunoblot and transcription products were monitored by autoradiography as described (Tang et al., *Cell* 154, 297-310, doi:10.1016/j.cell.2013.06.027 (2013)).

RNA-seq.

Total RNA was extracted from BMDM cells activated as indicated using a RNeasy Plus Mini Kit (74134, Qiagen, Hilden, Germany). Two to four micrograms of total RNA were used as starting material to prepare libraries using Illumina TruSeq Stranded mRNA Library Prep Kit Set A (RS-122-2101, Illumina, San Diego, CA). The libraries' size was selected by using the Agencourt AMPure XP beads (A63882, Beckman Coulter, Brea, CA), with average size of 400 bp. The libraries were sequenced using Illumina HiSeq 4000 (pair end 50 bp).

Bioinformatic analysis of RNA-seq data: Sequencing quality was evaluated by FastQC version 0.11.4. All reads were mapped to the reference genome of Illumina iGenomes UCSC mm10 using HISAT2 version 2.1.0. Differential expression analysis was implemented using edgeR version 3.16.5, after retaining only genes for which counts per million (cpm) was larger than one in four samples and normalizing the library sizes across samples using the TMM method of the edgeR package. Hierarchical clustering was performed and heat maps were generated using Perseus version 1.6.1.1 (http://www.coxdocs.orcq/doku.php?id=perseus:start). The Log 2 transformed gene expression values (Reads Per Kilobase of transcript, per Million mapped reads (RPKM)) were normalized by subtracting the mean in every row, and hierarchically clustered with a Pearson correlation algorithm. Gene Ontology analysis (GOTERM_BP_DIRECT) was carried out using DAVID Bioinformatics Resources 6.8.

The following primers were used for RT-qPCR analysis: Arg1:

```
                                 (SEQ ID NO: 93)
CTCCAAGCCAAAGTCCTTAGAG, (SEQ ID NO: 94)
AGGAGCTGTCATTAGGGACATC;

Vegfa:
                                 (SEQ ID NO: 95)
CCACGACAGAAGGAGAGCAGAAGTCC, (SEQ ID NO: 96)
CGTTACAGCAGCCTGCACAGCG;

Il6:
                                 (SEQ ID NO: 97)
GTTCTCTGGGAAATCGTGGA, (SEQ ID NO: 98)
TTTCTGCAAGTGCATCATCG;

Il1b:
                                 (SEQ ID NO: 99)
TTTGACAGTGATGAGAATGACC, (SEQ ID NO: 100)
CTCTTGTTGATGTGCTGCTG;

Ifnb1:
                                 (SEQ ID NO: 101)
CAGCTCCAAGAAAGGACGAAC, (SEQ ID NO: 102)
GGCAGTGTAACTCTTCTGCAT;

Cxcl10:
                                 (SEQ ID NO: 103)
CCAAGTGCTGCCGTCATTTTC, (SEQ ID NO: 104)
GGCTCGCAGGGATGATTTCAA;

Tnfa:
                                 (SEQ ID NO: 105)
CCCTCACACTCAGATCATCTTCT, (SEQ ID NO: 106)
GCTACGACGTGGGCTACAG.
```

ChIP-seq.

Native ChIP was carried out following the published protocol (Cuddapah et al., *Cold Spring Harb Protoc* 2009, pdb prot5237, doi:10.1101/pdb.prot5237 (2009)) with spiked-in for normalization purpose. Spike-in was carried out according to vendor protocols (#61686, Active motif, Carlsbad, CA). Briefly, 50 ng of Spike-in chromatin (#53083, Active motif, Carlsbad, CA) was added to 25 µg of BMDM chromatin to incubate with 2 µg Spike-in antibody (#61686, Active motif, Carlsbad, CA) together with 4 µg of anti-H3K18la or anti-H3K18ac antibodies. After 4 hours of incubation at 4° C., Protein A Sepharose (17-5280-01, GE Healthcare Life Sciences, Pittsburgh, PA) was added and incubated for another 2 hours, followed by sequential wash with buffer TSE I (0.1% SDS, 1% Triton X-100, 2 mM EDTA, 20 mM Tris-HCl pH 8.0, 150 mM NaCl), TSE II (0.1% SDS, 1% Triton X-100, 2 mM EDTA, 20 mM Tris-HCl pH 8.0, 500 mM NaCl), buffer III (0.25 M LiCl, 1% NP-40, 1% deoxycholate, 1 mM EDTA, 10 mM Tris-HCl pH 8.0), and TE buffer (1 mM EDTA, 10 mM Tris-HCl pH 8.0). Chromatin DNA was finally eluted with buffer containing 1% SDS and 0.1 M NaHCO$_3$. The eluates were digested with RNase A (12091021, Thermo Fisher Scientific, Waltham, MA) and proteinase K (AM2546, Thermo Fisher Scientific, Waltham, MA). DNA was recovered using the QIAquick PCR purification kit (#28106, Qiagen, Hilden, Germany) according to the manufacturer's instructions.

ChIP-seq libraries were constructed with an Accel-NGS 2S Plus DNA Library Kit (Swift Biosciences, Ann Arbor, MI) according to the manufacturer's protocol. The libraries were then amplified and assessed for fragment size using TapeStation (Agilent, Santa Clara, CA) and quantified using a Qubit dsDNA HS Assay Kit (Thermo Fisher Scientific, Waltham, MA). The indexed libraries were pooled and sequenced on a Hiseq4000 Sequencer (Illumina, San Diego, CA) using the 50-nt single-read configuration.

Bioinformatics analysis of ChIP-seq data: Sequencing quality was evaluated by FastQC version 0.11.4. All reads were mapped to the reference genome of Illumina iGenomes UCSC mm10 using Bowtie version 2.2.6, and only uniquely mapped reads were retained. Then SAMtools version 0.1.19 was used to convert files to bam format, sort, and remove PCR duplicates. Peaks were called using MACS version 2.2.1 under q value=0.01. To quantify and directly compare H3K18la or H3K18ac in different samples (M0 and M1 macrophages), the uniquely mapped H3K18la or H3K18ac reads in promoter regions (±2 kb around transcriptional start sites) of each gene were counted by featureCounts version 1.5.0-p1, and then normalized by Spike-in ChIP read counts of the corresponding condition (M0 or M1 macrophages). The overlap genes in ChIP-seq and RNA-seq data were used for all subsequent analysis. Gene Ontology analysis (GOTERM_BP_DIRECT) was carried out using DAVID Bioinformatics Resources 6.8.

The following primers were used for qPCR analysis of gene promoter regions in human cells:

```
FOXO3a-promoter:
                                 (SEQ ID NO: 107)
CAGTGAGTGTGTGCAGCTTG, (SEQ ID NO: 108)
AAAGCCTCCTGTTTGTGCTT;

FOXO3a-downstream:
                                 (SEQ ID NO: 109)
TGCACACAGAAGCCAGAAG, (SEQ ID NO: 110)
GCTCCCCACAGAGACGTAA;
```

LDHA-promoter:
TAAGGGTGGGGGATACCTCT, (SEQ ID NO: 111)

CCCAAGAGAAAAATGCAAGC. (SEQ ID NO: 112)

The following primers were used for qPCR analysis of gene promoter regions in mouse cells:

Arg1/Arg1-PTM:
AAGCTGTGGCCTCAGAACAT, (SEQ ID NO: 113)

GGTAACCGCTGTGAAAGGAT; (SEQ ID NO: 114)

Arg1-HRE-1kb:
CCCGAGTTTGACCCGAAGAA, (SEQ ID NO: 115)

CTTTACACAGGGACCGGACC; (SEQ ID NO: 116)

Arg1-HRE-2kb:
TGTCTCTCCCAGTTTCCCCA, (SEQ ID NO: 117)

AGCAACTTGGCATCTGATGGA; (SEQ ID NO: 118)

Vegfa/Vegfa-PTM:
CGAGCTAGCACTTCTCCCAG, (SEQ ID NO: 119)

AACTTCTGGGCTCTTCTCGC; (SEQ ID NO: 120)

Vegfa-HRE-1kb:
GGCACCAAATTTGTGGCACT, (SEQ ID NO: 121)

CTGCCAGACTACACAGTGCA; (SEQ ID NO: 122)

Vegfa-HRE-2kb:
ACCTGATCCTGATCCCTGCT, (SEQ ID NO: 123)

CAGCCTCTGTTATGCCACGA; (SEQ ID NO: 124)

Vegfa-HRE-3kb:
GCAGAACCTAGGCTTCACGT, (SEQ ID NO: 125)

TTGAAAGGGCTGACATGGCT; (SEQ ID NO: 126)

Eno1:
AAGGTCATCAGCAAGGTCGT, (SEQ ID NO: 127)

CGTACTCCGAGTCTCACACG; (SEQ ID NO: 128)

Glut1(Slc2a1):
TAGATCCCCTCCCTCTTGCT, (SEQ ID NO: 129)

GAACACGTAGCCTGCTCACA; (SEQ ID NO: 130)

Gene desert:
CTGCCAGGGTTGTAGAGAGG, (SEQ ID NO: 131)

GCCAGATCATATTGGCTTGG. (SEQ ID NO: 132)

Statistical Analysis.

No statistical methods were used to predetermine sample size. The significance of differences in the experimental data were determined using GraphPad Prism 7.0 software. All data involving statistics are presented as mean±s.e.m. For data presented without statistics, experiments were repeated at least three times to ensure reproducibility, unless otherwise stated.

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

---

What is claimed is:

1. A method for detecting a lactylated lysine in a protein or a fragment thereof, comprising:
    (a) contacting the protein or a fragment thereof with an affinity reagent selected from the group consisting of pan anti-Kla (PTM-1401) antibody, anti-H3K18la (PTM-1406) antibody, and anti-H4K5la (PTM-1407) antibody, whereby a binding complex of the protein or a fragment thereof and the affinity reagent is formed, and
    (b) detecting the binding complex, wherein the presence of the binding complex indicates the presence of a lactylated lysine in the protein or a fragment thereof.

2. The method of claim 1, wherein the binding of the affinity reagent to the peptide depends on a surrounding peptide sequence of the lactylated lysine in the peptide.

3. The method of claim 1, further comprising quantifying the lactylated lysine in the protein or a fragment thereof.

4. The method of claim 1, wherein the affinity reagent is pan anti-Kla (PTM-1401) antibody.

5. The method of claim 1, wherein the affinity reagent is anti-H3K18la (PTM-1406) antibody.

6. The method of claim 1, wherein the affinity reagent is anti-H4K5la (PTM-1407) antibody.

* * * * *